United States Patent
Musicki et al.

(10) Patent No.: US 10,287,278 B2
(45) Date of Patent: May 14, 2019

(54) CHEMOKINE CXCR1 AND CXCR2 RECEPTOR ANTAGONIST COMPOUNDS, AND USE THEREOF IN THE TREATMENT OF CHEMOKINE-MEDIATED PATHOLOGIES

(71) Applicant: GALDERMA RESEARCH & DEVELOPMENT, Biot (FR)

(72) Inventors: Branislav Musicki, Nice (FR); Yushma Bhurruth-Alcor, Antibes (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/539,590

(22) PCT Filed: Dec. 22, 2015

(86) PCT No.: PCT/FR2015/053703
§ 371 (c)(1),
(2) Date: Jun. 23, 2017

(87) PCT Pub. No.: WO2016/102877
PCT Pub. Date: Jun. 30, 2016

(65) Prior Publication Data
US 2017/0349575 A1    Dec. 7, 2017

(30) Foreign Application Priority Data

Dec. 23, 2014 (FR) ..................... 14 63209

(51) Int. Cl.
| | | |
|---|---|---|
| C07D 409/06 | (2006.01) | |
| C07D 213/75 | (2006.01) | |
| C07D 407/12 | (2006.01) | |
| C07C 381/10 | (2006.01) | |
| C07D 213/38 | (2006.01) | |
| C07D 307/52 | (2006.01) | |
| C07D 405/12 | (2006.01) | |

(52) U.S. Cl.
CPC .......... *C07D 409/06* (2013.01); *C07C 381/10* (2013.01); *C07D 213/38* (2013.01); *C07D 213/75* (2013.01); *C07D 307/52* (2013.01); *C07D 405/12* (2013.01); *C07D 407/12* (2013.01); *C07C 2601/04* (2017.05)

(58) Field of Classification Search
CPC .................................................... C07D 409/06
See application file for complete search history.

(56) References Cited

FOREIGN PATENT DOCUMENTS

| WO | 00/35442 A1 | 6/2000 |
|---|---|---|
| WO | 02/057230 A1 | 7/2002 |
| WO | 02/083624 A1 | 10/2002 |
| WO | 2008/148790 A1 | 12/2008 |
| WO | 2010/015613 A1 | 2/2010 |

OTHER PUBLICATIONS

International Search Report and Written Opinion dated Mar. 3, 2016 corresponding to International Patent Application No. PCT/FR2015/053703, 13 pages.

*Primary Examiner* — Paul V Ward
(74) *Attorney, Agent, or Firm* — Sunit Talapatra; Foley & Lardner LLP

(57) ABSTRACT

Novel chemokine CXCR1 and CXCR2 receptor antagonist compounds of general formula (I) are described. Also described, are pharmaceutical compositions including the compounds, and use of the compounds and the compositions for the treatment of chemokine-mediated pathologies, more specifically in the field of dermatology.

6 Claims, 2 Drawing Sheets

CHEMOKINE CXCR1 AND CXCR2 RECEPTOR ANTAGONIST COMPOUNDS, AND USE THEREOF IN THE TREATMENT OF CHEMOKINE-MEDIATED PATHOLOGIES

CROSS-REFERENCE TO PRIOR APPLICATIONS

This application is a National Stage of PCT/FR2015/053703, filed Dec. 22, 2015, and designating the United States (published on Jun. 30, 2016, as WO 2016/102877 A1), which claims priority under 35 U.S.C. § 119 to French Application No. 1463209, filed Dec. 23, 2014, each hereby expressly incorporated by reference in its entirety and each assigned to the assignee hereof.

FIELD OF THE INVENTION

The present invention relates to novel CXCR1 and CXCR2 chemokine receptor antagonist compounds, to pharmaceutical compositions containing these compounds and also to the use of these compounds and of these compositions for treating chemokine-mediated pathologies, more particularly in the field of dermatology.

PRIOR ART

Chemokines or cytokines are small soluble proteins. They are best known for their role in attracting and controlling the state of activation of immune system cells. All chemokines exert their functions by binding to receptors coupled to the G proteins. Certain chemokines are considered as pro-inflammatory. Secretion of these chemokines may be induced during the immune response so as to promote the arrival of immune system cells to a site of infection.

Two types of chemokines exist: pro-inflammatory chemokines and constitutive chemokines.

Pro-inflammatory (or "inducible") chemokines are produced at sites of inflammation by infiltrated leucocytes or tissue cells, after contact with a pathogen.

Constitutive (or "homeostatic") chemokines are produced by lymphoid organs and in certain non-lymphoid organs such as the skin and mucous membranes. They regulate the trafficking of lymphocytes and the localization of lymphocytes within these organs during lymphopoiesis, but also serve in maintaining immunosurveillance.

The nomenclature of these chemokine receptors is based on the chemokine group to which its ligand belongs. Thus, the receptors corresponding to the chemokines of the CXC group are known, for example, as CXCR1, CXCR2, CXCR3, CXCR4, etc., and the receptors corresponding to the chemokines of the CC group are known, for example, as CCR1, CCR2, CCR3, etc. These receptors all have a similar tertiary structure, and they are coupled to a G protein: they thus form part of the superfamily of GPCRs (G protein coupled receptor).

Interleukin-8 or IL-8 (also known as CXCL-8) is a member of the family of CXC chemokines, which plays a fundamental role in recruiting neutrophils to the site of inflammation. Two receptors, CXCR1 and CXCR2, are known to be specifically activated by IL-8. Whereas CXCR2 binds with strong affinity to IL-8 and to related chemokines such as CXCL6, CXCL5, CXCL3, CXCL2 and CXCL1, CXCR1 binds solely to IL-8. High levels of IL-8 and of related chemokines (CXCL5, CXCL2 and CXCL1) have been described in inflammatory acne lesions (J. Invest. Dermatol. 2006; 126: 1071-9; Am. J. Pathol. 2005; 166(6): 1691-9; Diagn. Pathol. 2007 Jan. 30; 2: 4).

First indications demonstrate the expression of CXCR2 in inflammatory acne (Trivedi et al., J. Invest. Dermatol. 2006 126(5): 1071-9). Thus, twofold antagonists of CXCR1 and CXCR2 might make it possible rapidly to reduce the deleterious effects of the IL-8 inflammatory response.

It is nowadays known that numerous inflammatory pathologies are mediated by chemokines.

In the field of dermatology, there is also a need, which to date remains unsatisfied, to treat the inflammatory component of pathologies of interest, for instance acne, rosacea or neutrophilic dermatoses, especially psoriasis.

The Applicant has now discovered novel compounds with antagonist activity towards receptors of CXCR1 and CXCR2 type and which are characterized by the presence in their structure of a functional group, of sulfoximine type, corresponding to the substructure (Ia) below:

In comparison with their closest structural analogues, taken from the prior art, for example in document WO02/083624, and containing a functional group of sulfone type in place of the functional group of sulfoximine type, these compounds have better antagonist activity towards receptors of CXCR1 and CXCR2 type.

They also show, unexpectedly, better inhibition of migration of neutrophils to the site of inflammation when compared with their closest structural analogues, taken, for example, from document WO02/083624, which gives them an additional advantage over the compounds already known in the treatment of chemokine-mediated pathologies, and more particularly of dermatological pathologies.

SUMMARY OF THE INVENTION

A first subject according to the invention relates to novel CXCR1 and CXCR2 chemokine receptor antagonist compounds, and also to the salts and enantiomers thereof, corresponding to the general formula (I) below:

in which the groups A and B and the substituents R3, R4 and R5 are as defined below in the detailed description of the invention.

A second subject according to the invention relates to a pharmaceutical composition comprising an effective amount of a compound corresponding to the general formula (I) in combination with a pharmaceutically acceptable support or solvent.

A third subject according to the invention relates to a compound or a pharmaceutical composition as described above for its use as a medicament.

A fourth subject according to the invention relates to a compound or a pharmaceutical composition as described above for its use in the treatment of chemokine-mediated diseases.

A fifth subject according to the invention relates to a compound or a pharmaceutical composition as described above for its use in the treatment of chemokine-mediated diseases selected from the group comprising neutrophilic dermatoses, and especially psoriasis, atopic dermatitis, acne, rosacea, asthma, chronic obstructive pulmonary disease, adult respiratory diseases, arthritis, inflammatory bowel diseases, Crohn's disease, graft rejection, mucoviscidosis and skin cancers.

The invention also relates to a method for treating chemokine-mediated diseases, comprising the administration of an effective amount of a compound or of a pharmaceutical composition as defined in the present patent application to a patient suffering from a chemokine-mediated disease.

The invention also relates to the use of a compound or of a pharmaceutical composition as defined in the present patent application, for the preparation of a medicament for treating chemokine-mediated diseases.

DETAILED DESCRIPTION OF THE INVENTION

Figure 1:
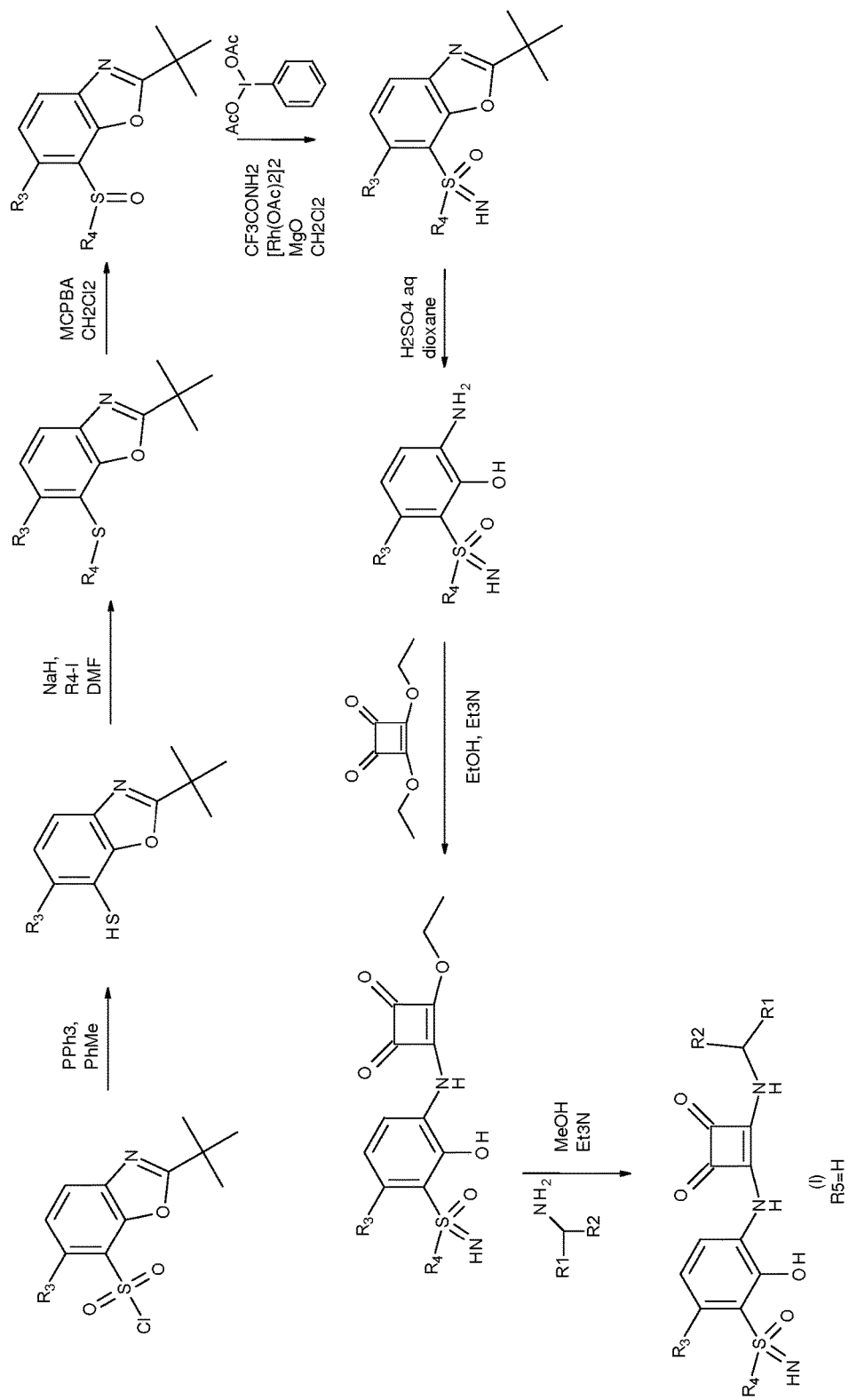
FIG. 1 represents the general synthetic scheme for preparing the compounds of general formula (I) in which R5 represents a hydrogen and B represents (B1).

Unless otherwise indicated, the following definitions apply to all of the description and of the claims.

These definitions apply independently of knowing whether a term is used alone or in combination with other terms. Thus, for example, the definition of the term "aryl" applies equally to "aryl" per se and to the "aryl" part of the term "aryloxy" or "arylalkyl".

"Alkyl" denotes a linear or branched saturated hydrocarbon-based chain in which the number of carbon atoms is specified.

When the number of carbon atoms is not specified, this means that the alkyl chain contains from 1 to 20 carbon atoms.

The preferred alkyl radicals contain from 1 to 12 carbon atoms, and the even more preferred radicals contain from 1 to 6 carbon atoms in the chain.

"Alkoxy" denotes an oxygen substituted with an alkyl radical as defined previously. Examples of alkoxy radicals include methoxy, ethoxy, n-propoxy, isopropoxy and n-butoxy radicals.

"Aryl" denotes a monocyclic or polycyclic (2 to 3 rings) aromatic ring system comprising from 6 to 14 carbon atoms and preferably from 6 to 10 carbon atoms.

Examples of aryl radicals that may be mentioned include phenyl, naphthyl, indenyl, tetrahydronaphthyl, indanyl, anthracenyl and fluorenyl radicals.

The preferred aryl radicals are the phenyl radical and the naphthyl radical. The even more preferred aryl radical is the phenyl radical.

"Heteroaryl" denotes a monocyclic or polycyclic (2 to 3 rings) aromatic system comprising from 5 to 14 ring atoms, preferably from 5 to 10 ring atoms, in which one or more of the ring atoms represent(s) one or more (from 1 to 5) heteroatoms chosen from the group comprising nitrogen, oxygen and sulfur.

The preferred heteroaryls contain 5 or 6 ring atoms and 1 to 3 heteroatoms.

The prefix aza, oxa or thia before the name of the heteroaryl root means that at least one nitrogen, one oxygen or one sulfur, respectively, is present in the ring.

A nitrogen atom of a heteroaryl may optionally be oxidized to N-oxide. As examples of suitable heteroaryls, mention may be made of the following heteroaryls: pyridyl, pyrazinyl, furyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolyl, imidazolyl, thienopyridyl, quinazolinyl, thienopyrimidyl, pyrrolopyridyl, imidazopyridyl, isoquinolyl, benzazaindolyl, 1,2,4-triazinyl and benzothiazolyl.

The preferred heteroaryl radicals are chosen from the following list: pyridyl, pyrazinyl, furyl, thienyl, pyrimidinyl, isoxazolyl, isothiazolyl, oxazolyl, thiazolyl, pyrazolyl, furazanyl, pyrrolyl, pyrazolyl, triazolyl.

The even more preferred heteroaryl radicals are the pyridyl radical and the furyl radical.

"Arylalkyl" denotes a radical in which the aryl and alkyl parts are as defined above. Examples of arylalkyls that may be mentioned include benzyl, phenethyl and naphthalenylmethyl radicals.

The bonding to the structure to which it is attached takes place via the alkyl radical.

"Heteroarylalkyl" denotes a radical in which the heteroaryl and alkyl parts are as defined above.

Examples of heteroarylalkyls that may be mentioned include pyridylmethyl, pyridylethyl, imidazolylmethyl, imidazolylethyl, pyrazolylmethyl and pyrazolylethyl radicals.

The bonding to the structure to which it is attached takes place via the alkyl radical.

"Cycloalkyl" denotes a non-aromatic hydrocarbon-based ring system, containing from 3 to 10 carbon atoms, preferably from 5 to 10 carbon atoms, and from one to three rings.

The preferred cycloalkyl radicals contain from 5 to 7 ring atoms.

Examples of cycloalkyl radicals that may be mentioned include cyclopropyl, cyclopentyl, cyclohexyl, cycloheptyl, norbornyl and adamantyl radicals.

"Cycloalkylalkyl" denotes a radical in which the cycloalkyl and alkyl parts are as defined above.

Examples of cycloalkylalkyls that may be mentioned include cyclopropylmethyl, cyclopropylethyl, cyclobutylmethyl, cyclobutylethyl, cyclopentylmethyl, cyclopentylethyl, cyclohexylmethyl, cyclohexylethyl, norbornylmethyl and adamantylmethyl radicals.

The bonding to the structure to which it is attached takes place via the alkyl radical.

"Heterocycloalkyl" denotes a non-aromatic hydrocarbon-based ring system, containing from 4 to 10 carbon atoms, preferably from 5 to 10 carbon atoms, and from one to three rings, and comprising from one to three heteroatoms chosen from the group consisting of nitrogen, oxygen and sulfur.

The preferred heterocycloalkyl radicals contain from 5 to 7 ring atoms.

Examples of heterocycloalkyl radicals that may be mentioned include tetrahydrofuryl, tetrahydrothienyl, tetrahydropyranyl, piperidyl and 7-oxabicyclo[2.2.1]heptanyl radicals.

"Fluoroalkyl" denotes an alkyl radical as defined previously, substituted with one or more fluorine atoms.

Examples of fluoroalkyl radicals that may be mentioned include fluoromethyl, difluoromethyl, 2-fluoroethyl, 2,2-difluoroethyl and 2,2,2-trifluoroethyl radicals.

"Perfluoroalkyl" denotes an alkyl radical as defined previously in which each hydrogen atom has been replaced with a fluorine atom.

Examples of perfluoroalkyl radicals that may be mentioned include trifluoromethyl and pentafluoroethyl radicals.

"Halogen" denotes a fluorine, chlorine, bromine or iodine atom. The preferred halogens are fluorine and chlorine atoms.

"Pharmaceutically acceptable salt" denotes the salts of a compound of interest which have the desired biological activity. The pharmaceutically acceptable salts comprise salts of acidic or basic groups present in the specified compounds. The pharmaceutically acceptable acid-addition salts comprise, but are not limited to, hydrochloride, hydrobromide, hydriodide, nitrate, sulfate, bisulfate, phosphate, hydrogen phosphate, isonicotinate, acetate, lactate, salicylate, citrate, tartrate, pantothenate, bitartrate, ascorbate, succinate, maleate, gentisate, fumarate, gluconate, glucuronate, saccharate, formate, benzoate, glutamate, methanesulfonate, ethanesulfonate, benzenesulfonate, p-toluenesulfonate and pamoate (i.e. 1,1'-methylenebis(2-hydroxy-3-naphthoate)) salts. Salts of suitable bases comprise, but are not limited to, aluminium, calcium, lithium, magnesium, potassium, sodium, zinc and diethanolamine salts. A list of pharmaceutically acceptable salts is especially published in the review by Berge et al. (*J. Pharm. Sci.* 1977, 66(1), 1-19).

Thus, a first subject according to the invention relates to novel CXCR1 and CXCR2 chemokine receptor antagonist compounds, and also to the salts and enantiomers thereof, corresponding to the general formula (I) below:

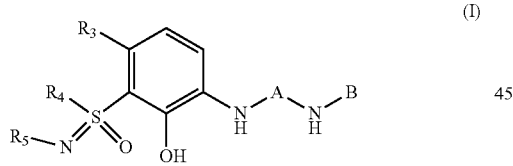
(I)

in which:
A represents

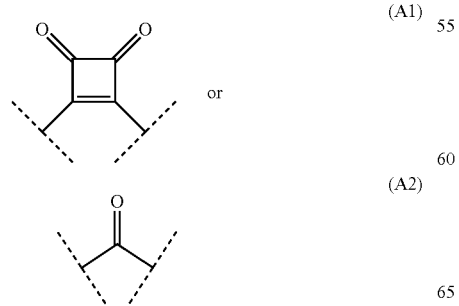
(A1) or (A2)

B represents

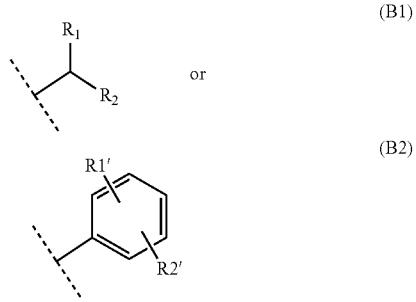
(B1) or (B2)

with

R1' and R2', which may be identical or different, represent a hydrogen, a halogen, a C1 to C5 alkyl which is unsubstituted or substituted with one or more fluorine atoms, a C1 to C5 alkoxy, OCF3, OH, CN or NR11R12, R1 and R2, which may be identical or different, represent:
- a hydrogen,
- a C1 to C5 alkyl, which is unsubstituted or substituted with one or more groups chosen from F, OH, OCH3 and NR11R12; R11 and R12 having the meaning given below, it being understood that when the C1 to C5 alkyl radical is substituted only with one or more fluorine atoms, it is a C1 to C5 fluoroalkyl radical or perfluoroalkyl radical,
- a C1 to C5 alkyl in which a carbon atom is replaced with an oxygen atom or with a sulfur atom, said C1 to C5 alkyl being unsubstituted or substituted with one or more groups chosen from F, OH and NR11R12, R11 and R12 having the meaning given below,
- a C3 to C8 cycloalkyl radical,
- a C2 to C5 alkyne, which is unsubstituted or substituted with one or more groups chosen from F, OH, phenyl and NR11R12, R11 and R12 having the meaning given below,
- a cycloalkyl corresponding to one of the formulae (1), (2), (3), (4), (5) or (6) below in which R5', X and X' have the meanings given below:

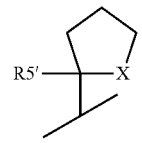
(1)

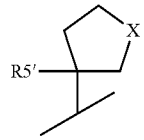
(2)

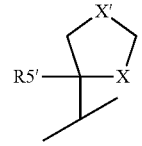
(3)

(4)
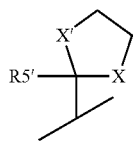

(5)
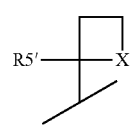

(6)
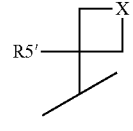

an aromatic or heteroaromatic ring selected from the group consisting of the rings corresponding to formulae (a) to (o) below in which R7, R7a, Y and Z have the meanings given below:

(a)
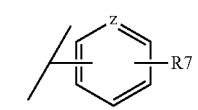

(b)
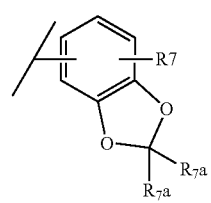

(c)
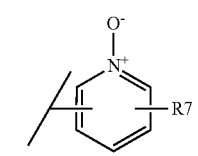

(d)
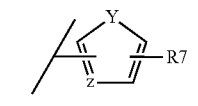

(e)
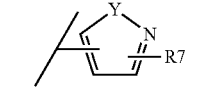

(f)
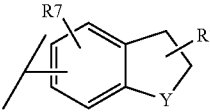

(g)
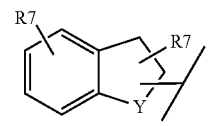

(h)
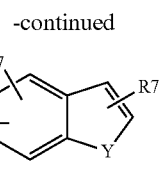

(i)
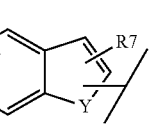

(j)

(k)

(l)

(m)

(n)

(o)

R7 may be present several times on a ring, and at most as many times as there are substitutable atoms; the meanings of each substituent R7 may be identical or different, R3 represents a hydrogen, a halogen, a C1 to C5 alkyl, a C1 to C5 alkoxy, —CF3, —OCF3, —OH, —NO2 or CN, R4 and R5, which may be identical or different, represent:
a hydrogen,
a C1 to C8 alkyl, which is unsubstituted or substituted with one or more groups chosen from F, OH and NR11R12, R11 and R12 having the meaning given below,
a C1 to C8 alkyl in which a carbon atom is replaced with a nitrogen atom, with an oxygen atom or with a sulfur atom, said C1 to C8 alkyl being unsubstituted or substituted with one or more groups chosen from F, OH and NR11R12, R11 and R12 having the meaning given below,
a C3 to C8 cycloalkyl radical,
a C3 to C8 cycloalkyl radical, one of the carbon atoms of which is replaced with an oxygen atom or with a nitrogen atom substituted with a radical R7a, a heterocycloalkyl of 5 to 7 ring atoms,
a cycloalkylalkyl, the cycloalkyl being C3 to C8 and the alkyl C1 to C8,
a phenyl,
a phenyl substituted with a radical R7,
a heteroaryl,
an arylalkyl, the alkyl being C1-C5,
a heteroarylalkyl, the alkyl being C1-C5, or alternatively
R4 and R5 represent a chain (CH$_2$)$_m$— forming a ring containing from 5 to 8 atoms with the sulfur and nitrogen atoms to which they are respectively attached, one of the carbons of the ring being optionally replaced with an oxygen or sulfur atom or with a nitrogen atom substituted with a radical R8; m and R8 having the meanings given below,
R5' represents a hydrogen atom, a fluorine, an alkyl radical comprising from 1 to 5 carbon atoms inclusive or a fluoroalkyl or perfluoroalkyl radical comprising from 1 to 5 carbon atoms,
R6 represents a hydrogen atom, a radical COOtBu or a radical COOBn,
R7 represents a hydrogen, a C1 to C3 alkyl, a halogen, —CF3, —COR9, —OR9, —NR9R10, —NO2, —CN, —SO2R9, —S(O)R9, —S(=O)(=NR9)R10', —SO2NR9R10, —NR9SO2R10, —NR9COR10, —NR9CO2R10, —CONR9R10 or —CO2R9,
R7a represents a hydrogen or a C1 to C5 alkyl,
R8 represents a hydrogen, —OH, —SO2R9, —COR9, —CO2R9, an aryl, a heteroaryl, an arylalkyl, a heteroarylalkyl, an alkyl, a cycloalkyl or alternatively a cycloalkylalkyl,
R9 and R10 are identical or different and are chosen independently from the group consisting of a hydrogen, an aryl, a heteroaryl, an arylalkyl, a heteroarylalkyl, an alkyl, a cycloalkyl or a cycloalkylalkyl,
or alternatively
R9 and R10 may be linked together when they are borne by the same nitrogen atom so as to form a 3- to 7-membered heterocycle comprising one or two heteroatoms chosen from oxygen, sulfur and nitrogen in addition to the nitrogen atom to which they are attached,
R10' represents an aryl, a heteroaryl, an arylalkyl, a heteroarylalkyl, an alkyl, a cycloalkyl or a cycloalkylalkyl,
R11 and R12, which may be identical or different, represent a hydrogen, a C1 to C5 alkyl, a C3 to C6 cycloalkyl, a chain (CH$_2$)$_p$— forming a ring containing from 4 to 6 atoms with the nitrogen atom to which they are attached,
X and X', which may be identical or different, represent an oxygen atom, a sulfur atom or a nitrogen atom substituted with a radical R6,
Y represents an oxygen atom, a sulfur atom or a nitrogen atom substituted with a radical R8,
Z represents a carbon atom or a nitrogen atom,
m=3, 4, 5 or 6 and
p=3, 4 or 5.

In a particularly preferred embodiment according to the invention, the compounds correspond to the general formula (I) in which:
A represents

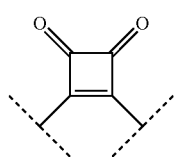

(A1)

B represents

(B1)

R1 represents a hydrogen, a C1 to C5 alkyl, which is unsubstituted or substituted with one or more groups chosen from F, OH and OCH3, a C3 to C8 cycloalkyl radical, or a cycloalkyl corresponding to formula (1') below in which X has the meaning given below:

(1')

R2 represents:
a C1 to C5 alkyl, which is unsubstituted or substituted with one or more groups chosen from F, it being understood that when the C1 to C5 alkyl radical is substituted only with one or more fluorine atoms, it is a C1 to C5 fluoroalkyl radical or perfluoroalkyl radical,
a C1 to C5 alkyl in which a carbon atom is replaced with an oxygen atom,
a C2 to C5 alkyne, which is unsubstituted or substituted with one or more groups chosen from fluorine and phenyl,
an aromatic or heteroaromatic ring selected from the group consisting of the rings corresponding to formulae (a), (b1) and (d1) below in which R7 and Z have the meanings given below:

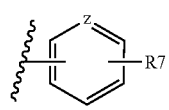

(a)

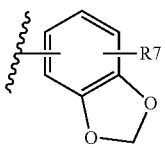

(b1)

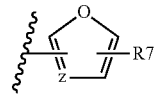

(d1)

R7 may be present several times on a ring, and at most as many times as there are substitutable atoms; the meanings of each substituent R7 may be identical or different,
R3 represents a hydrogen or a chlorine,
R4 and R5, which may be identical or different, represent:
a hydrogen,
a C1 to C3 alkyl, which is unsubstituted or substituted with a group NR11R12, R11 and R12 having the meaning given below, a C1 to C8 alkyl in which a carbon atom is replaced with an oxygen atom,
a pyridyl,
a piperidyl, R7 represents a hydrogen, a C1 to C3 alkyl or a fluorine, X represents a sulfur atom, and Z represents a carbon atom or a nitrogen atom.

In a more particularly preferred embodiment according to the invention, the compounds correspond to the general formula (I) in which:

A represents

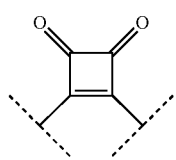

(A1)

B represents

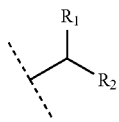

(B1)

R1 represents a hydrogen, a C1 to C5 alkyl, a C3 to C8 cycloalkyl radical, or a cycloalkyl corresponding to formula (1') below in which X has the meaning given below:

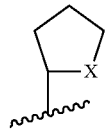

(1')

R2 represents:
a C1 to C5 alkyl, which is unsubstituted or substituted with one or more groups chosen from F, it being understood that when the C1 to C5 alkyl radical is substituted only with one or more fluorine atoms, it is a C1 to C5 fluoroalkyl radical or perfluoroalkyl radical, a C1 to C5 alkyl in which a carbon atom is replaced with an oxygen atom, a C2 to C5 alkyne, which is unsubstituted or substituted with one or more groups chosen from fluorine and phenyl, an aromatic or heteroaromatic ring selected from the group consisting of the rings corresponding to formulae (a), (b1) and (d1) below in which R7 and Z have the meanings given below:

(a)

(b1)

(d1)

R7 may be present several times on a ring, and at most as many times as there are substitutable atoms; the meanings of each substituent R7 may be identical or different, R3 represents a hydrogen or a chlorine, R4 and R5, which may be identical or different, represent a hydrogen, a C1 to C3 alkyl, or a C1 to C8 alkyl in which a carbon atom is replaced with an oxygen atom, R7 represents a hydrogen, a C1 to C3 alkyl or a fluorine, X represents a sulfur atom, and Z represents a carbon atom or a nitrogen atom.

The compounds corresponding to the more particularly preferred embodiment as described above have CXCR1 receptor antagonist activities of less than 400 nM and CXCR2 receptor antagonist activities of less than 100 nM.

These compounds, in the sulfoximine series, have activity higher than that of their structurally closest analogues of the prior art in the sulfone series as illustrated below by way of example:

TABLE 1

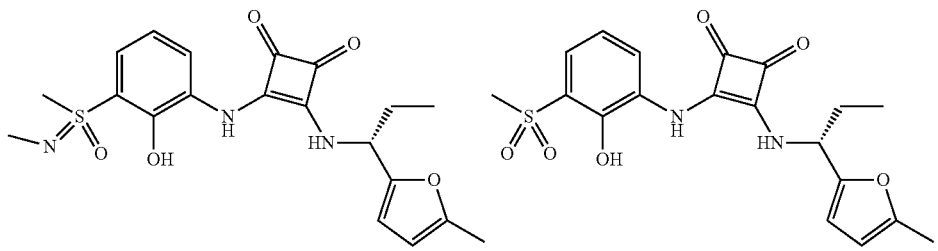

| | Example 16 | WO02/083624 |
|---|---|---|
| CXCR1 IC50 (nM) | 36 | 418 |
| CXCR2 IC50 (nM) | 18 | 103 |

TABLE 1-continued

| 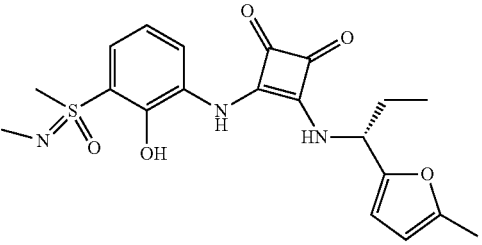 | 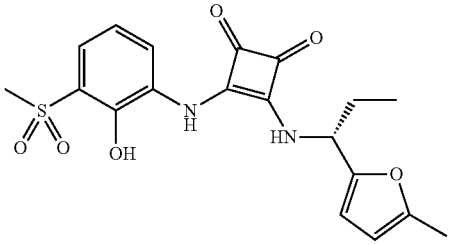 |
|---|---|
| Example 16 | WO02/083624 |
| Migration of h neutrophils IC50 (nM) | 356 | 3090 |

In the most preferred embodiment according to the invention, the compounds correspond to the abovementioned general formula (I) in which:

A represents

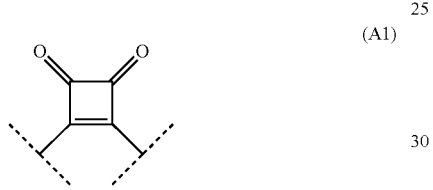
(A1)

B represents

(B1)

R1 represents a C1 to C5 alkyl,

R2 represents:
- a C1 to C5 alkyl,
- a C2 to C5 alkyne, substituted with one or more groups chosen from fluorine and phenyl,
- an aromatic or heteroaromatic ring selected from the group consisting of the rings corresponding to formulae (a), (b1) and (d1) below in which R7 and Z have the meanings given below:

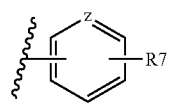
(a)

-continued

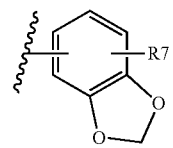
(b1)

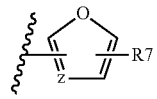
(d1)

R7 may be present several times on a ring, and at most as many times as there are substitutable atoms; the meanings of each substituent R7 may be identical or different, R3 represents a hydrogen or a chlorine, R4 and R5, which may be identical or different, represent a hydrogen or a C1 to C3 alkyl, R7 represents a hydrogen, a C1 to C3 alkyl or a fluorine, and Z represents a carbon atom or a nitrogen atom.

The compounds corresponding to the most preferred embodiment as described above have CXCR1 receptor antagonist activities of less than 50 nM and CXCR2 receptor antagonist activities of less than 20 nM.

These compounds, in the sulfoximine series, have activity higher than that of their closest analogues of the prior art in the sulfone series as illustrated below by way of example:

TABLE 2

|  | Example 12 | WO02/083624 |
|---|---|---|
| CXCR1 IC50 (nM) | 28 | 155 |
| CXCR2 IC50 (nM) | 16 | 66 |
| Migration of h neutrophils IC50 (nM) | 82 | 831 |

In another embodiment according to the invention, the compounds correspond to the general formula (I) in which:

A represents

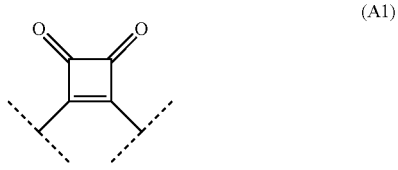

(A1)

B represents

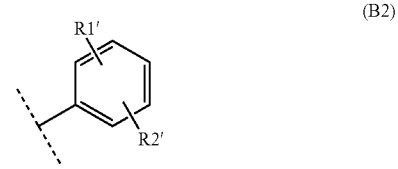

(B2)

R1' and R2', which may be identical or different, represent a hydrogen, a chlorine or a fluorine,
R3 represents a hydrogen or a chlorine,
R4 and R5, which may be identical or different, represent a hydrogen or a C1 to C3 alkyl.

Among the most particularly preferred compounds, examples that may be mentioned include those chosen from the list comprising:

Compound 1: 3-(4-chloro-2-hydroxy-3-methanesulfoxyiminophenylamino)-4-[(R)-1-(5-methylfuran-2-yl)propylamino]cyclobut-3-ene-1,2-dione Compound 2: 3-{4-chloro-2-hydroxy-3-methane[(N-methyl)sulfoximino]phenylamino}-4-[(R)-1-(5-methylfuran-2-yl)propylamino]cyclobut-3-ene-1,2-dione Compound 3: 3-{4-chloro-2-hydroxy-3-methane[(N-pyridin-4-yl)sulfoximino]-phenylamino}-4-[(R)-1-(5-methylfuran-2-yl)propylamino]cyclobut-3-ene-1,2-dione Compound 4: 3-{4-chloro-2-hydroxy-3-methane[(N-pyridin-4-yl)sulfoximino]-phenylamino}-4-(1-ethylpropylamino)cyclobut-3-ene-1,2-dione Compound 5: 3-{4-chloro-2-hydroxy-3-methane[(N-methyl)sulfoximino]phenylamino}-4-{[(S)-(5-methylfuran-2-yl)(R)-tetrahydrothiophen-2-ylmethyl]amino}cyclobut-3-ene-1,2-dione Compound 6: 1-(2-chloro-3-fluorophenyl)-3-(4-chloro-2-hydroxy-3-methanesulfoximinophenyl)urea Compound 7: 1-(2-chloro-3-fluorophenyl)-3-{4-chloro-2-hydroxy-3-methane[(N-methyl)sulfoximino]phenyl}urea Compound 8: 3-{12-hydroxy-3-methane[(N-methyl)sulfoximino]phenylamino}-4-[(R)-1-(5-methylfuran-2-yl)propylamino]cyclobut-3-ene-1,2-dione Compound 9: 3-[4-chloro-3-[N-(2-dimethylaminoethyl)-S-methylsulfonimidoyl]-2-hydroxyanilino]-4-ethoxycyclobut-3-ene-1,2-dione Compound 10: 3-[4-chloro-3-[N-(2-dimethylaminoethyl)-S-methylsulfonimidoyl]-2-hydroxyanilino]-4-(1-ethylpropylamino)cyclobut-3-ene-1,2-dione Compound 11: 3-[4-chloro-2-hydroxy-3-[N-(2-methoxyethyl)-S-methylsulfonimidoyl]anilino]-4-[[(1R)-1-(5-methyl-2-furyl)propyl]amino]cyclobut-3-ene-1,2-dione Compound 12: (−)-3-{4-chloro-2-hydroxy-3-methane[(N-methyl)sulfoximino]-phenylamino}-4-[(R)-1-(pyridin-2-yl)propylamino]cyclobut-3-ene-1,2-dione Compound 13: (+)-3-{4-chloro-2-hydroxy-3-methane[(N-methyl)sulfoximino]-phenylamino}-4-[(R)-1-(pyridin-2-yl)propylamino]cyclobut-3-ene-1,2-dione Compound 14: (−)-3-{12-hydroxy-3-methane[(N-methyl)sulfoximino]phenylamino}-4-[(R)-1-(pyridin-2-yl)propylamino]cyclobut-3-ene-1,2-dione Compound 15: (−)-3-{12-hydroxy-3-methane[(N-methyl)sulfoximino]phenylamino}-4-[(R)-1-(pyridin-2-yl)propylamino]cyclobut-3-ene-1,2-dione Compound 16: (+)-3-{2-hydroxy-3-methane[(N-methyl)sulfoximino]phenylamino}-4-[(R)-1-(5-methylfuran-2-yl)propylamino]cyclobut-3-ene-1,2-dione Compound 17: (+)-3-{2-hydroxy-3-methane[(N-methyl)sulfoximino]phenylamino}-4-[(R)-1-(5-methylfuran-2-yl)propylamino]cyclobut-3-ene-1,2-dione Compound 18: (−)-3-(2-hydroxy-3-methane[(N-methyl)sulfoximino]phenylamino[4-(1-ethylpropylamino]cyclobut-3-ene-1,2-dione Compound 19: (+)-3-(2-hydroxy-3-methane[(N-methyl)sulfoximino]phenylamino[4-(1-ethylpropylamino]cyclobut-3-ene-1,2-dione Compound 20: (+)-3-{4-chloro-2-hydroxy-3-methane[(N-methyl)sulfoximino]-phenylamino}-4-[(R)-1-(5-methylfuran-2-yl)propylamino]cyclobut-3-ene-1,2-dione.

A second subject according to the invention relates to a pharmaceutical composition comprising an effective amount of a compound corresponding to the general formula (I) as described above in combination with a solvent or a pharmaceutically acceptable support.

A third subject according to the invention relates to compounds corresponding to the general formula (I), and also the salts and enantiomers thereof, or alternatively a pharmaceutical composition comprising an effective amount of a compound corresponding to the general formula (I), or a salt or enantiomer thereof, for their use as medicaments.

A fourth subject according to the invention relates to compounds corresponding to the general formula (I), and also the salts and enantiomers thereof, or alternatively a pharmaceutical composition comprising an effective amount of a compound corresponding to the general formula (I), or a salt or enantiomer thereof, for their use in the treatment of α-chemokine-mediated diseases.

As examples of α-chemokine-mediated diseases, mention may be made of neutrophilic dermatoses, especially psoriasis, atopic dermatitis, acne, rosacea, asthma, chronic obstructive pulmonary disease, adult respiratory diseases, arthritis, inflammatory bowel diseases, Crohn's disease, graft rejection, mucoviscidosis and skin cancers.

The term "neutrophilic dermatoses" means, in its broadest sense, Sweet's syndrome, "eccrine hydradenitis", SAPHO syndrome, Sneddon-Wilkinson syndrome, pyoderma gangrenosum, erythema elevatum duitinum, psoriasis, common psoriasis, pustular psoriasis, palmoplantar pustulosis, exanthematous pustulosis (AGEP), vasculitis pustulosis, infantile acropustulosis, Behcet's disease, and also certain bullous diseases such as herpes derived in the form of dermatitis, neutrophilic IgA dermatosis, intraepidermal IgA pustulosis, bullous pemphigoid, IgA pemphigus, vasculitis, Leroy-Reiter-Fiellinger syndrome, pustulosis of the scalp, Hallopeau's continuous acrodermatitis and dermatoses associated with angio-immunoblastic lymphoadenopathy, with cyclophosphamide-induced dysmyelopoiesis, with p-ANCA antibodies.

In a preferred embodiment of the invention, the compound or the pharmaceutical composition mentioned above is used for treating dermatalogical diseases such as neutrophilic dermatoses, especially psoriasis, atopic dermatitis, acne and rosacea.

Another aspect of the invention relates to the use of a compound corresponding to the general formula (I), and also the salts and enantiomers thereof, or alternatively to the use of a pharmaceutical composition comprising an effective amount of a compound corresponding to the general formula (I), a salt thereof and an enantiomer thereof, for the preparation of a medicament for treating diseases of the group comprising neutrophilic dermatoses, especially psoriasis, atopic dermatitis, acne, rosacea, asthma, chronic obstructive pulmonary disease, adult respiratory diseases, arthritis, inflammatory bowel diseases, Crohn's disease and skin cancers.

Figure 2:
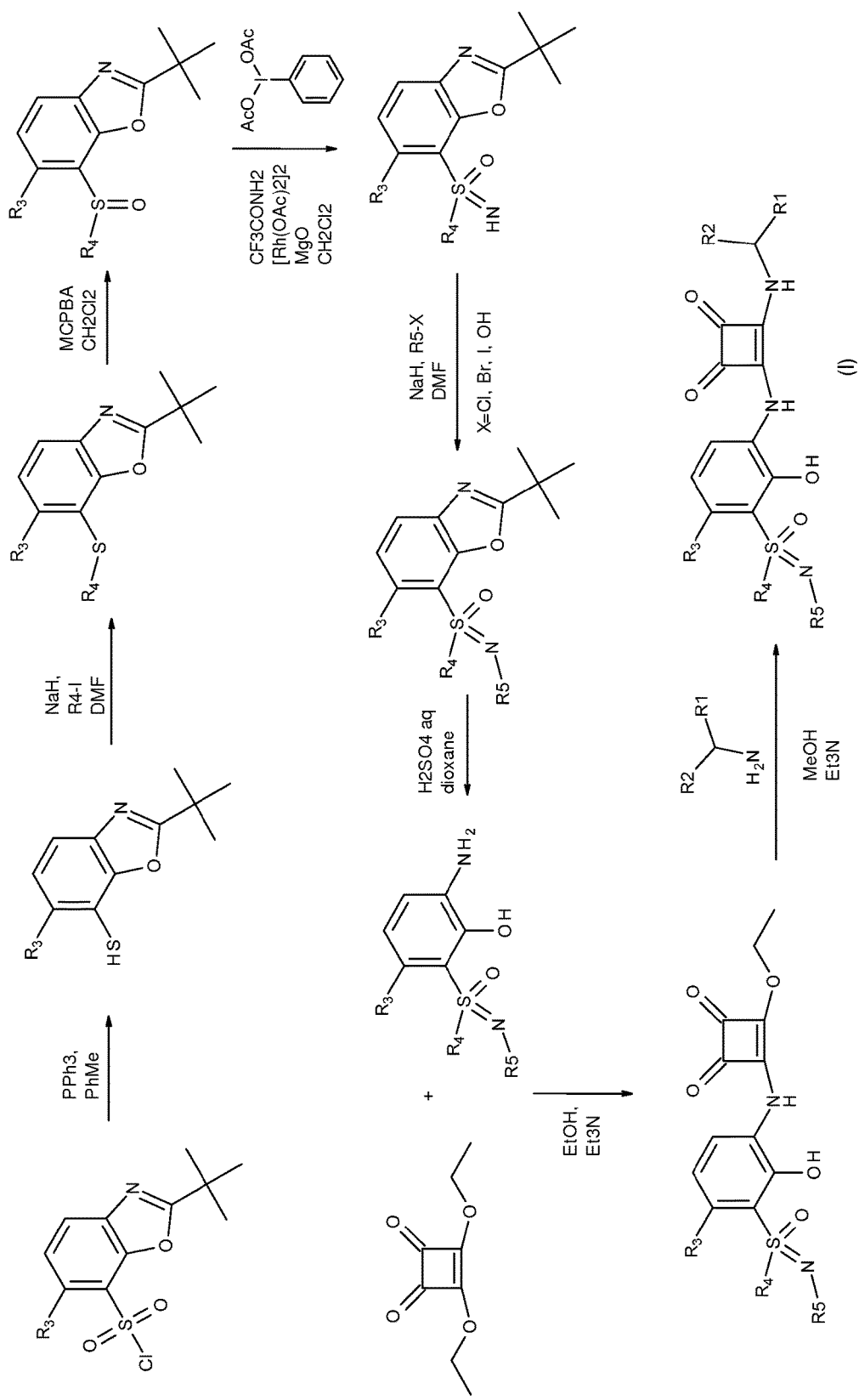
FIG. 2 represents the general synthetic scheme for preparing the compounds of general formula (I) in which R5 is other than hydrogen and B represents (B1).

The compounds of general formula (I) of the present invention are prepared according to one of the two synthetic routes as emerge from the synthetic schemes indicated in FIGS. 1 and 2. A person skilled in the art will be able readily to deduce the experimental conditions required for each of these two synthetic routes by referring to those used for each synthetic route as emerge from the examples for the preparation of the compounds of formula (I) illustrated in a non-limiting manner below.

By way of illustration, the following compounds, corresponding to the general formula (I) of the present invention, were prepared by following one of the two schemes presented above and in FIGS. 1 and 2.

Preparation of the Compounds of Formula (I)

Example 1

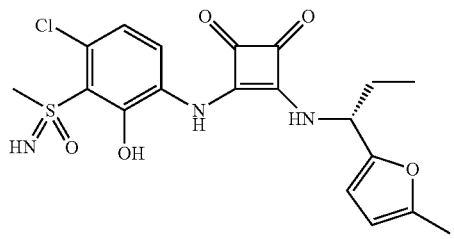

3-(4-Chloro-2-hydroxy-3-methanesulfoximinophenylamino)-4-[(R)-1-(5-methylfuran-2-yl)propylamino]cyclobut-3-ene-1,2-dione To a suspension of 3-(4-chloro-2-hydroxy-3-methanesulfoximinophenylamino)-4-ethoxycyclobut-3-ene-1,2-dione (0.19 g; 0.51 mmol) in methanol (8 ml) are added a solution of (R)-1-(5-methylfuran-2-yl)propylane hydrochloride (0.11 g; 0.62 mmol) in methanol (1 ml) and triethylamine (85 µl; 0.62 mmol). After three days, the reaction medium is partially concentrated. Ethyl acetate and then aqueous 1M sodium dihydrogen phosphate solution are added. The organic phase is washed again with aqueous 1M sodium dihydrogen phosphate solution. The solid obtained is chromatographed on silica gel (eluent: heptane/acetone, from 20% to 70% acetone). 3-(4-Chloro-2-hydroxy-3-methanesulfoximinophenylamino)-4-[(R)-1-(5-methylfuran-2-yl)propylamino]cyclobut-3-ene-1,2-dione (0.12 g; 50%) is obtained.

Melting point: 192° C. MS (ES+) m/z 438 (MH+).

1H NMR (400 MHz, DMSO-$d_6$): δ 0.92 (td, J=7.3, 1.5 Hz, 3H); 1.90-1.92 (m, 2H); 2.27 (s, 3H); 3.64 (s, 3H); 5.13 (q, J=7.8 Hz, 1H); 6.06 (dd, J=3.1, 1.3 Hz, 1H); 6.27 (t, J=2.6 Hz, 1H); 7.02 (d, J=8.7 Hz, 1H); 8.03 (dd, J=8.7, 2.0 Hz, 1H); 8.76 (dd, J=9.0, 3.9 Hz, 1H); 9.36 (d, J=3.7 Hz, 1H); 11.72 (s, 2H).

3-(4-Chloro-2-hydroxy-3-methanesulfoximinophenylamino)-4-ethoxycyclobut-3-ene-1,2-dione To a solution of 6-amino-3-chloro-2-methanesulfoximinophenol (0.52 g; 2.12 mmol) in ethanol (35 ml) is added 3,4-diethoxy-3-cyclobutene-1,2-dione (0.63 ml; 4.24 mmol). The reaction medium is heated for 3 days at 60° C. and is then concentrated. The oil obtained is chromatographed on silica gel (eluent: heptane/acetone, from 10% to 80% acetone). 3-(4-Chloro-2-hydroxy-3-methanesulfoximinophenylamino)-4-ethoxycyclobut-3-ene-1,2-dione (0.39 g; 49%) is obtained. MS (ES+) m/z 345/347 (MH+).

6-Amino-3-chloro-2-methanesulfoximinophenol

To a solution of 2-tert-butyl-6-chloro-7-methanesulfoximinobenzoxazole (0.80 g; 2.79 mmol) in 1,4-dioxane (4 ml) are added water (1 ml) and sulfuric acid (0.95 ml; 17.77 mmol). The reaction medium is then heated to 100° C. After 1 hour 40 minutes, the reaction medium is cooled and hydrolysed with 1N sodium hydroxide solution and water is added (up to pH=6-7). The mixture is extracted with ethyl acetate. The organic phase is dried over anhydrous sodium sulfate, filtered and concentrated. 6-Amino-3-chloro-2-methanesulfoximinophenol (0.55 g; 80%) is obtained. MS (ES+) m/z 221/223 (MH+).

2-tert-Butyl-6-chloro-7-methanesulfoximinobenzoxazole

To a suspension of 2-tert-butyl-6-chloro-7-methanesulfinylbenzoxazole (11.11 g; 40.88 mmol), 2,2,2-trifluoroacetamide (9.24 g; 81.76 mmol) and magnesium oxide (6.59 g; 163.52 mmol) in dichloromethane (400 ml) degassed for about 15 minutes under nitrogen are added rhodium(II) acetate dimer (1.45 g; 3.27 mmol) and iodobenzene diacetate (20.15 g; 62.55 mmol). After 17 hours, 2,2,2-trifluoroacetamide (2.50 g; 22.12 mmol), iodobenzene diacetate (3.48 g; 10.80 mmol) and rhodium(II) acetate dimer (0.69 g; 1.56 mmol) are added. After 20 hours, the reaction medium is heated to reflux. After 45 hours, the reaction medium is filtered through Celite and is concentrated. The residue is taken up in methanol (400 ml) and potassium carbonate (28.25 g; 204.40 mmol) is added. After 1 hour, the reaction medium is concentrated. The residue is taken up in ethyl acetate and washed with water. The aqueous phase is again extracted with ethyl acetate. The organic phases are combined, dried over anhydrous sodium sulfate, filtered and concentrated. The oil obtained is chromatographed on silica gel (eluent: heptane/ethyl acetate, from 5% to 80% ethyl acetate). 2-tert-Butyl-6-chloro-7-methanesulfoximinobenzoxazole (1.76 g; 15%) is obtained. MS (ES+) m/z 287/289 (MH+).

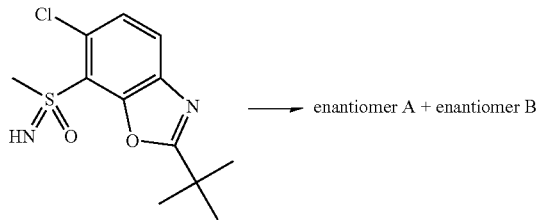 [SMILES: CC(C)(C)c1nc2ccc(Cl)c(S(C)(=N)=O)c2o1]

→ enantiomer A + enantiomer B (−)-2-tert-Butyl-6-chloro-7-methanesulfoximinobenzoxazole (enantiomer A) (+)-2-tert-Butyl-6-chloro-7-methanesulfoximinobenzoxazole (enantiomer B)

2-tert-Butyl-6-chloro-7-methanesulfoximinobenzoxazole (2.5 g) was separated into enantiomers via the chiral HPLC method on a CHIRALCEL OJ 20 µm LC50 column with 90/10 heptane/ethanol solvent as eluent. The separation gave enantiomer A (1.35 g, retention time 11.71 min, $[\alpha]_D$=−2.4° (c=10 g/L, EtOH)) and enantiomer B (1.37 g, retention time 23.10 min, $[\alpha]_D$=+3.5° (c=10 g/L, EtOH)).

2-tert-Butyl-6-chloro-7-methanesulfinylbenzoxazole

To a solution of 2-tert-butyl-6-chloro-7-methylsulfanylbenzoxazole (9.78 g; 38.24 mmol) in dichloromethane (200 ml) under nitrogen is added portionwise 3-chloroperbenzoic acid (9 g; 40.15 mmol). After 24 hours, the reaction medium is hydrolysed with 2N sodium hydroxide. The organic phase is washed a second time with 2N sodium hydroxide solution. The organic phase is dried over anhydrous sodium sulfate, filtered and concentrated. 2-tert-Butyl-6-chloro-7-methanesulfinylbenzoxazole (11.9 g; 100%) is obtained. MS (ES+) m/z 272/274 (MH+).

2-tert-Butyl-6-chloro-7-methylsulfanylbenzoxazole

To a suspension of sodium hydride at 60% in oil (2.20 g; 55.00 mmol) in tetrahydrofuran (135 ml), under nitrogen, in a bath at 0° C. are added, dropwise, a solution of 2-tert-butyl-6-chlorobenzoxazole-7-thiol (12 g; 49.64 mmol) in tetrahydrofuran (60 ml) followed 15 minutes later by iodomethane (9.5 ml; 152.60 mmol). The reaction medium is then returned to room temperature. After 16 hours, aqueous 1M sodium dihydrogen phosphate solution and ethyl acetate are added. The organic phase is dried over anhydrous sodium sulfate, filtered and concentrated. The oil obtained is chromatographed on silica gel (eluent: heptane/ethyl acetate, from 0% to 10% ethyl acetate). 2-tert-Butyl-6-chloro-7-methylsulfanylbenzoxazole (10.85 g; 85%) is obtained. MS (ES+) m/z 256/258 (MH+).

2-tert-Butyl-6-chlorobenzoxazole-7-thiol

To a solution of 2-tert-butyl-6-chlorobenzoxazole-7-sulfonyl chloride (15.01 g; 48.70 mmol) under nitrogen in toluene (250 ml) is added a solution of triphenylphosphine (38.32 g; 146.11 mmol) in toluene (125 ml) (the reaction is exothermic). After 40 minutes, the reaction medium is hydrolysed with water (250 ml) and left stirring for 1 hour. The organic phase is then extracted twice with 1N sodium hydroxide solution (2×125 ml). The basic aqueous phases are combined and washed twice with toluene (2×125 ml). The aqueous phase is then acidified to pH=1 with aqueous 2N hydrochloric acid solution and is then extracted twice with dichloromethane (2×150 ml). The organic phases are combined, dried over anhydrous sodium sulfate, filtered and concentrated. 2-tert-Butyl-6-chlorobenzoxazole-7-thiol (11.37 g; 96%) is obtained. MS (ES+) m/z 342/344 (MH+).

Example 2

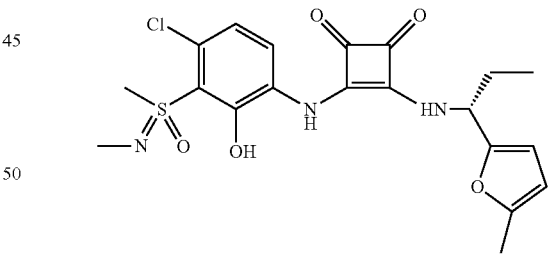

3-{4-Chloro-2-hydroxy-3-methane[(N-methyl)sulfoximino]phenylamino}-4-[(R)-1-(5-methylfuran-2-yl)propylamino]cyclobut-3-ene-1,2-dione To a mixture of 3-(4-chloro-2-hydroxy-3-methane[(N-methyl)sulfoximino]-phenylamino)-4-ethoxycyclobut-3-ene-1,2-dione (0.16 g; 0.45 mmol) in methanol (3 ml) are added a solution of (R)-1-(5-methylfuran-2-yl)propylane hydrochloride (90 mg; 0.51 mmol) in methanol (1 ml) and triethylamine (70 µl; 0.50 mmol). The reaction medium is then heated to 50° C. After 2 hours, ethyl acetate is added and the reaction medium is washed twice with aqueous 1M sodium dihydrogen phosphate solution. The organic phase is dried over anhydrous sodium sulfate, filtered and concentrated. The solid obtained is dried under vacuum in an oven at 50° C. 3-{4-Chloro-2-hydroxy-3-methane[(N-methyl)sulfoximino]phenylamino}-4-[(R)-1-(5-methylfuran-2-yl)propylamino]cyclobut-3-ene-1,2-dione (0.18 g; 88%) is obtained; melting point: 131° C. MS (ES+) m/z 452 (MH+)

1H NMR (400 MHz, DMSO-d$_6$): δ 0.92 (td, J=7.3, 1.4 Hz, 3H); 1.90-1.92 (m, 2H); 2.27 (s, 3H); 2.91 (s, 3H); 3.70 (s, 3H); 5.13 (q, J=7.7 Hz, 1H); 6.06 (dd, J=3.0, 1.2 Hz, 1H); 6.26 (t, J=2.6 Hz, 1H); 6.98 (d, J=8.7 Hz, 1H); 8.05 (dd, J=8.7, 2.2 Hz, 1H); 8.78 (dd, J=9.0, 3.6 Hz, 1H); 9.36 (d, J=3.7 Hz, 1H).

3-(4-Chloro-2-hydroxy-3-methane[(N-methyl)sulfoximino]phenylamino)-4-ethoxycyclobut-3-ene-1,2-dione To a solution of 6-amino-3-chloro-2-methane[(N-methyl)sulfoximino]phenol (0.39 g; 1.33 mmol) in ethanol (35 ml) is added 3,4-diethoxy-3-cyclobutene-1,2-dione (0.50 ml; 3.38 mmol). The reaction medium is heated to 60° C. After three days, the reaction medium is concentrated. The oil obtained is chromatographed on silica gel (eluent: heptane/acetone, from 20% to 50% acetone). 3-(4-Chloro-2-hydroxy-3-methane[(N-methyl)sulfoximino]phenylamino)-4-ethoxycyclobut-3-ene-1,2-dione (0.32 g; 67%) is obtained. MS (ES+) m/z 359/361 (MH+).

6-Amino-3-chloro-2-methane[(N-methyl)sulfoximino]phenol

To a solution of 2-tert-butyl-6-chloro-7-methane-N-methylsulfoximinobenzoxazole (0.50 g; 1.66 mmol) in 1,4-dioxane (2.5 ml) are added water (0.60 ml) and concentrated sulfuric acid dropwise (0.57 ml; 10.66 mmol). The reaction medium is heated at 100° C. for 1 h 30 min, and then for 2 hours at 70° C. and then returned to 100° C. After reaction for 4 hours, concentrated sulfuric acid (0.20 ml; 3.74 mmol) is added. After reaction for 7 hours, concentrated sulfuric acid (0.40 ml; 7.48 mmol) is again added. After 8 hours, the reaction medium is hydrolysed with water and aqueous 1N sodium hydroxide solution is added (up to pH=7). The mixture is extracted with ethyl acetate. The organic phase is dried over anhydrous sodium sulfate, filtered and concentrated. 6-Amino-3-chloro-2-methane[(N-methyl)sulfoximino]phenol (0.39 g; 80%) is obtained. MS (ES+) m/z 235/237 (MH+).

2-tert-Butyl-6-chloro-7-methane-N-methylsulfoximinobenzoxazole

To a suspension of sodium hydride at 60% in oil (0.12 g; 3.00 mmol) in N,N-dimethylformamide (15 ml) at 0° C. under nitrogen is added a solution of 2-tert-butyl-6-chloro-7-methanesulfoximinobenzoxazole (0.74 g; 2.58 mmol) in N,N-dimethylformamide (15 ml). 20 minutes later, iodomethane (0.32 ml; 5.14 mmol) is added. The reaction medium is then returned to room temperature. After 3 hours 30 minutes, the reaction medium is hydrolysed with water and extracted with ethyl acetate. The organic phase is washed once again with water, dried over anhydrous sodium sulfate, filtered and concentrated. The oil obtained is chromatographed on silica gel (eluent: heptane/ethyl acetate, from 30% to 80% ethyl acetate). 2-tert-Butyl-6-chloro-7-methane-N-methylsulfoximinobenzoxazole (0.51 g; 65%) is obtained. MS (ES+) m/z 301/303 (MH+).

Example 3

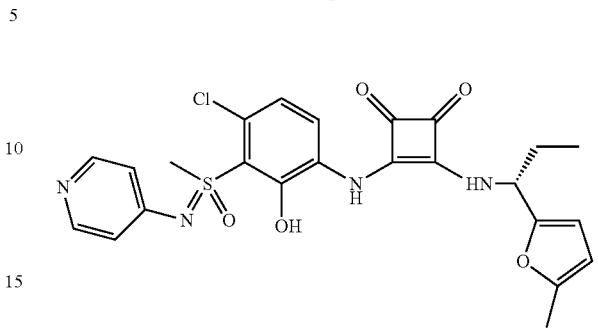

3-{4-Chloro-2-hydroxy-3-methane[(N-pyridin-4-yl)sulfoximino]phenylamino}-4-[(R)-1-(5-methylfuran-2-yl)propylamino]cyclobut-3-ene-1,2-dione To a suspension of 3-(4-chloro-2-hydroxy-3-methane[(N-pyridin-4-yl)sulfoximino]-phenylamino)-4-ethoxycyclobut-3-ene-1,2-dione (114 mg; 0.27 mmol) and (R)-1-(5-methylfuran-2-yl)propylane hydrochloride (54.59 mg; 0.31 mmol) in methanol (3 ml) is added triethylamine (0.04 ml; 0.31 mmol). The reaction medium is heated at 60° C. for 24 hours. The cooled reaction medium is diluted with dichloromethane and washed twice with aqueous 1M sodium dihydrogen phosphate solution. The organic phase is dried over anhydrous magnesium sulfate, filtered and concentrated. The solid obtained is taken up in methanol and crystallized from ether. The compound is chromatographed on silica gel, eluting with 95/5 dichloromethane/methanol. 3-{4-Chloro-2-hydroxy-3-methane[(N-pyridin-4-yl)sulfoximino]phenylamino}-4-[(R)-1-(5-methylfuran-2-yl)propylamino]cyclobut-3-ene-1,2-dione is obtained (70 mg; 48%). MS (ES+) m/z 515 (MH+).

1H NMR (400 MHz, DMSO-d$_6$): δ (ppm) 0.87-0.92 (m, 3H); 1.81 (dt, J=14.0, 7.0 Hz, 1H); 1.89-1.94 (m, 1H); 2.25 (d, J=6.7 Hz, 3H); 3.79 (s, 3H); 5.11 (q, J=7.6 Hz, 1H); 6.00-6.03 (m, 1H); 6.20 (t, J=4.3 Hz, 2H); 6.98 (dd, J=7.0, 2.2 Hz, 2H); 7.78 (d, J=8.2 Hz, 1H); 8.23 (dd, J=6.7, 4.6 Hz, 2H); 8.86 (d, J=9.0 Hz, 1H); 9.41 (s, 1H).

3-(4-Chloro-2-hydroxy-3-methane[(N-pyridin-4-yl)sulfoximino]phenylamino)-4-ethoxycyclobut-3-ene-1,2-dione To a solution of 6-amino-3-chloro-2-methane[(N-methyl)sulfoximino]phenol (222 mg; 0.75 mmol) in ethanol (20 ml) is added 3,4-diethoxy-3-cyclobutene-1,2-dione (0.30 ml; 2.01 mmol). The reaction medium is heated at 60° C. overnight. The reaction medium is concentrated and taken up in ethyl acetate and then in ether. 3-(4-Chloro-2-hydroxy-3-methane[(N-pyridin-4-yl)sulfoximino]phenylamino)-4-ethoxycyclobut-3-ene-1,2-dione is obtained (228 mg; 72%). MS (ES+) m/z 422 (MH+).

6-Amino-3-chloro-2-methane[(N-pyridin-4-yl)sulfoximino]phenol

Sulfuric acid (0.87 ml; 16.20 mmol) diluted in water (1.28 ml) at room temperature is added dropwise to 2-tert-butyl-6-chloro-7-(N-pyridin-4-yl)sulfoximinobenzoxazole (320 mg; 0.88 mmol) dissolved in 1,4-dioxane (5 ml). The reaction medium is stirred at 100° C. for 4 hours. The pH of the medium is brought to pH=7-8 with 1N sodium hydroxide, followed by extraction with ethyl acetate. The organic phase is dried, filtered and concentrated. 6-Amino-3-chloro-2-methane[(N-pyridin-4-yl)sulfoximino]phenol is obtained (222 mg; 84%). MS (ES+) m/z 298 (MH+).

2-tert-Butyl-6-chloro-7-(N-pyridin-4-yl)sulfoximinobenzoxazole

A mixture of 4-bromopyridine hydrochloride (848 mg; 4.36 mmol), 2-tert-butyl-6-chlorobenzoxazole-7-sulfoximine (1.00 g; 3.49 mmol), palladium acetate (39.14 mg; 0.17 mmol), 97% rac-2,2'-bis(diphenylphosphino)-1,1'-binaphthyl (21.71 mg; 0.03 mmol) and caesium carbonate (2.84 g; 8.72 mmol) in toluene (12.5 ml) (degassed) is heated at 110° C. for 40 hours. The reaction medium is taken up in water and the organic phase is extracted three times with ethyl acetate, dried and concentrated. The crude product is chromatographed on silica gel, eluent: from 70/30 to 40/60 dichloromethane/ethyl acetate. 2-tert-Butyl-6-chloro-7-(N-pyridin-4-yl)sulfoximinobenzoxazole is obtained (0.36 g; 28%).

MS (ES+) m/z 364 (MH+).

Example 4

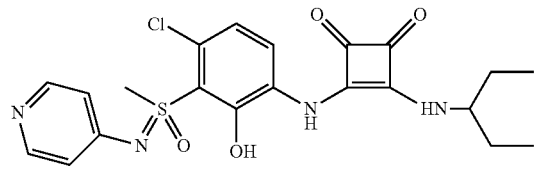 [SMILES: CCC(CC)Nc1c(Nc2ccc(Cl)c(S(C)(=O)=Nc3ccncc3)c2O)c(=O)c1=O]

3-{4-Chloro-2-hydroxy-3-methane[(N-pyridin-4-yl)sulfoximino]phenylamino}-4-(1-ethylpropylamino)cyclobut-3-ene-1,2-dione A suspension of 3-(4-chloro-2-hydroxy-3-methane[(N-pyridin-4-yl)sulfoximino]-phenylamino)-4-ethoxycyclobut-3-ene-1,2-dione (114 mg; 0.27 mmol) and 1-ethylpropylamine (0.04 ml; 0.32 mmol) in methanol (3 ml) is heated at 60° C. for 24 hours. The reaction medium is cooled. The precipitate formed is filtered off and dried. The compound obtained is chromatographed on silica gel, eluting with 95/5 dichloromethane/methanol. 3-{4-Chloro-2-hydroxy-3-methane[(N-pyri din-4-yl)sulfoximino]phenylamino}-4-(1-ethylpropylamino)cyclobut-3-ene-1,2-dione is obtained (85 mg; 67%).

1H NMR (400 MHz, DMSO-$d_6$): δ (ppm) 0.84-0.89 (m, 6H); 1.38-1.47 (m, 2H); 1.54-1.61 (m, 2H); 3.80 (s, 3H); 3.86 (t, J=7.3 Hz, 1H); 6.20 (s, 1H); 6.99 (d, J=6.8 Hz, 2H); 7.81 (d, J=8.2 Hz, 1H); 8.24 (d, J=6.8 Hz, 2H); 8.37 (d, J=9.1 Hz, 1H); 9.33 (s, 1H). MS (ES+) m/z 463 (MH+)

Example 5

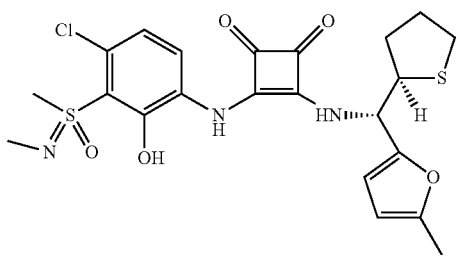 [SMILES: CN=S(C)(=O)c1c(Cl)ccc(Nc2c(N[C@@H](c3ccc(C)o3)[C@H]3CCCS3)c(=O)c2=O)c1O]

3-{4-Chloro-2-hydroxy-3-methane[(N-methyl)sulfoximino]phenylamino}-4-{[(S)-(5-methylfuran-2-yl)-(R)-tetrahydrothiophen-2-ylmethyl]amino}cyclobut-3-ene-1,2-dione To a mixture of 3-(4-chloro-2-hydroxy-3-methane[(N-methyl)sulfoximino]-phenylamino)-4-ethoxycyclobut-3-ene-1,2-dione (0.16 g; 0.45 mmol) in methanol (3 ml) is added a solution of C—[(S)—C-(5-methylfuran-2-yl)-C—(R)-tetrahydrothiophen-2-yl]methylamine (0.12 g; 0.61 mmol; prepared according to the procedure described in WO 2013/061 004) in methanol (1 ml). After 26 hours, ethyl acetate is added and the mixture is washed twice with aqueous 1M sodium dihydrogen phosphate solution. The organic phase is dried over anhydrous sodium sulfate, filtered and concentrated. The solid obtained is chromatographed on silica gel (eluent: heptane/acetone, from 10% to 50% acetone). The solid obtained is dried under vacuum in an oven at 50° C. 3-{4-Chloro-2-hydroxy-3-methane[(N-methyl)sulfoximino]phenylamino}-4-{[(S)-(5-methylfuran-2-yl)-(R)-tetrahydrothiophen-2-ylmethyl]amino}cyclobut-3-ene-1,2-dione (0.14 g; 61%) is obtained; melting point: 155° C. MS (ES+) m/z 510 (MH+).

1H NMR (400 MHz, DMSO-$d_6$): δ 1.81-1.85 (m, 1H); 1.91-1.94 (m, 1H); 2.01-2.06 (m, 2H); 2.27 (s, 3H); 2.79-2.81 (m, 2H); 2.90 (s, 3H); 3.70 (s, 3H); 3.87 (dt, J=9.6, 6.1 Hz, 1H); 5.20 (t, J=9.6 Hz, 1H); 6.07 (d, J=3.0 Hz, 1H); 6.30 (d, J=3.1 Hz, 1H); 6.98 (d, J=8.7 Hz, 1H); 8.03 (dd, J=8.7, 3.3 Hz, 1H); 8.89 (dd, J=9.6, 4.6 Hz, 1H); 9.41 (d, J=4.0 Hz, 1H).

Example 6

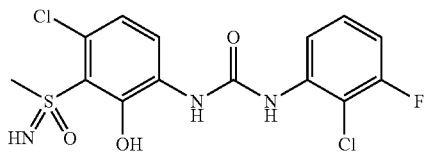 [SMILES: CS(=N)(=O)c1c(Cl)ccc(NC(=O)Nc2cccc(F)c2Cl)c1O]

1-(2-Chloro-3-fluorophenyl)-3-(4-chloro-2-hydroxy-3-methanesulfoximinephenyl)-urea To a solution of 6-amino-3-chloro-2-methanesulfoximinophenol (0.19 g; 0.81 mmol) in acetonitrile (1.50 ml) and N,N-dimethylformamide (0.50 ml), under nitrogen, is added a solution of 2-chloro-1-fluoro-3-isocyanatobenzene (0.15 g; 0.89 mmol) in acetonitrile (1 ml). After 2 hours, the reaction medium is concentrated. The residue is purified by preparative HPLC/MS (XSelect C18 column 21 mm in diameter, water/acetonitrile, 45% acetonitrile followed by 60%). 1-(2-Chloro-3-fluorophenyl)-3-(4-chloro-2-hydroxy-3-methanesulfoximinephenyl)urea (0.08 g; 25.2%) is obtained; melting point: 203° C. MS (ES−) m/z 390 (MH−).

1H NMR (400 MHz, DMSO-$d_6$): δ 3.63 (s, 3H); 7.00 (d, J=8.8 Hz, 1H); 7.08 (t, J=8.7 Hz, 1H); 7.34 (q, J=7.6 Hz, 1H); 7.98 (d, J=8.5 Hz, 1H); 8.28 (d, J=8.8 Hz, 1H); 9.27 (s, 1H); 9.30 (s, 1H); 11.64 (br s, 2H).

Example 7

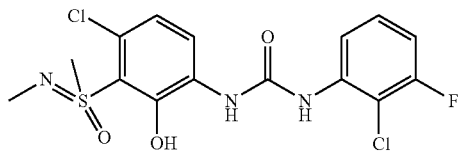 [SMILES: CN=S(C)(=O)c1c(Cl)ccc(NC(=O)Nc2cccc(F)c2Cl)c1O]

1-(2-Chloro-3-fluorophenyl)-3-{4-chloro-2-hydroxy-3-methane[(N-methyl) sulfoximino]phenyl}urea To a solution of 6-amino-3-chloro-2-methane[(N-methyl)sulfoximino]phenol (0.16 g; 0.52 mmol) in acetonitrile (1.5 ml) and N,N-dimethylformamide (0.50 ml) is added a solution of 2-chloro-1-fluoro-3-isocyanatobenzene (0.12 g; 0.68 mmol) in acetonitrile (1.5 ml). After 3 hours, the reaction medium is concentrated. The residue obtained is chromatographed on silica gel (eluent: heptane/ethyl acetate, from 10% to 60% ethyl acetate). 1-(2-Chloro-3-fluorophenyl)-3-{4-chloro-2-hydroxy-3-methane[(N-methyl)sulfoximino]phenyl}urea (0.10 g; 45%) is obtained; melting point: 107° C. MS (ES+) m/z 406 (MH+).

1H NMR (400 MHz, DMSO-$d_6$): δ 2.92 (s, 3H); 3.68 (s, 3H); 6.99 (d, J=8.8 Hz, 1H); 7.08 (t, J=8.7 Hz, 1H); 7.33-7.34 (m, 1H); 7.97 (d, J=8.5 Hz, 1H); 8.28 (d, J=8.8 Hz, 1H); 9.27 (s, 1H); 9.30 (s, 1H); 16.33 (br s, 1H).

Example 8

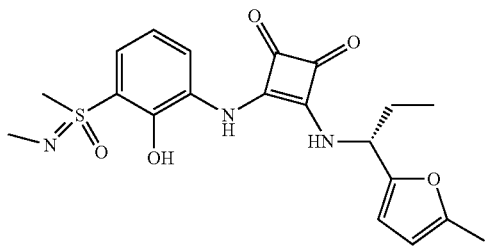

3-{2-Hydroxy-3-methane[(N-methyl)sulfoximino]phenylamino}-4-[(R)-1-(5-methylfuran-2-yl)propylamino]cyclobut-3-ene-1,2-dione To a suspension of 3-[3-(N,S-dimethylsulfonimidoyl)-2-hydroxyanilino]-4-ethoxycyclobut-3-ene-1,2-dione (0.10 g; 0.31 mmol) in methanol (3 ml) are added at room temperature (R)-1-(5-methylfuran-2-yl)propylane hydrochloride (64.99 mg; 0.37 mmol) and triethylamine (51 μl; 0.37 mmol). The reaction medium is heated at 60° C. for 1 hour 30 min. The reaction medium is concentrated and the crude product is chromatographed on silica gel (eluent: 10-60% methanol in dichloromethane). 3-{2-Hydroxy-3-methane[(N-methyl)sulfoximino]phenylamino}-4-[(R)-1-(5-methylfuran-2-yl)propylamino]cyclobut-3-ene-1,2-dione (0.10 g; 77) is obtained. MS (ES+) m/z 418 (MH+)

$^1$H NMR (DMSO-$d_6$) δ: 9.36 (s, 1H), 8.72 (dd, J=9.0, 2.2 Hz, 1H), 8.04 (dt, J=8.0, 1.7 Hz, 1H), 7.40 (dd, J=8.2, 1.5 Hz, 1H), 6.90 (t, J=8.0 Hz, 1H), 6.26 (t, J=2.2 Hz, 1H), 6.06 (d, J=3.6 Hz, 1H), 5.14 (q, J=7.9 Hz, 1H), 3.46 (s, 3H), 2.83 (s, 3H), 2.27 (s, 3H), 2.02-1.81 (m, 2H), 0.93 (t, J=7.3 Hz, 3H).

3-[3-(N,S-Dimethylsulfonimidoyl)-2-hydroxyanilino]-4-ethoxycyclobut-3-ene-1,2-dione To a solution of 2-amino-6-(N,S-dimethylsulfonimidoyl)phenol (0.53 g; 2.65 mmol) in ethanol (10 ml) is added at room temperature 3,4-diethoxy-3-cyclobutene-1,2-dione (0.59 ml; 3.97 mmol). The reaction medium is heated at 60° C. for 24 hours. The reaction medium is filtered and 0.39 g of expected product is recovered in the form of a yellow solid. 3-[3-(N,S-Dimethylsulfonimidoyl)-2-hydroxyanilino]-4-ethoxycyclobut-3-ene-1,2-dione (0.39 g; 45%) is obtained. MS (ES+) m/z 325 (MH+).

2-Amino-6-(N,S-dimethylsulfonimidoyl)phenol

To a solution of 2-tert-butyl-7-methane-N-methylsulfoximinobenzoxazole (0.57 g; 2.14 mmol) in 1,4-dioxane (8.6 ml) and water (2.28 ml) is added at room temperature sulfuric acid (2.11 ml; 39.42 mmol). The reaction medium is stirred at 100° C. for 4 hours and then for 16 hours at 80° C. The pH of the medium is brought to pH=7 with 10N sodium hydroxide, followed by extraction with 50 ml of ethyl acetate. The organic phase is recovered and then dried with magnesium sulfate, filtered and evaporated. 2-Amino-6-(N,S-dimethylsulfonimidoyl)phenol (0.54 g) is obtained. MS (ES+) m/z 201 (MH+).

2-tert-Butyl-7-methane-N-methylsulfoximinobenzoxazole

To a solution of 2-tert-butyl-6-chlorobenzoxazole-7-sulfoximine (550 mg; 2.18 mmol) in N,N-dimethylformamide (11 ml) is added portionwise sodium hydroxide at 60% in oil (105 mg; 2.62 mmol). The reaction medium is stirred for 20 minutes at room temperature and iodomethane (258 μl; 4.14 mmol) is then added. The reaction medium is then returned to room temperature and stirred for 20 minutes. The reaction medium is partitioned between 50 ml of water and 50 ml of ethyl acetate. The organic phase is washed twice with 20 ml of saturated sodium bicarbonate and dried over magnesium sulfate, filtered and evaporated. 2-tert-Butyl-7-methane-N-methylsulfoximinobenzoxazole (570 mg; 98%) is obtained. MS (ES+) m/z 267 (MH+).

2-tert-Butyl-7-methanesulfoximinobenzoxazole

To a solution, degassed 3 times, of 2-tert-butyl-6-chlorobenzoxazole-7-sulfoximine (1.00 g; 3.49 mmol) in tetrahydrofuran (18 ml) is added palladium(II) acetate (39.14 mg; 0.17 mmol), potassium fluoride (405.16 mg; 6.97 mmol) diluted in degassed water (7 ml) and 1,1,1,3,5,5,5-heptamethyltrisiloxane (3.10 g; 13.95 mmol), dropwise. The medium is stirred at room temperature for 1 hour. The medium is purged with nitrogen, and palladium acetate (39.14 mg; 0.17 mmol) and 1,1,1,3,5,5,5-heptamethyltrisiloxane (3.10 g; 13.95 mmol) are then added and the medium is stirred for 16 hours at room temperature. The medium is purged again with nitrogen, and palladium acetate (39.14 mg; 0.17 mmol), 1,1,1,3,5,5,5-heptamethyltrisiloxane (3.10 g; 13.95 mmol) and potassium fluoride (405.16 mg; 6.97 mmol) are then added and the medium is stirred for 30 minutes at room temperature. The medium is transferred onto 30 ml of 3N NaOH at 0° C. and then stirred for 4 hours at room temperature. The medium is extracted 3 times with 50 ml of diethyl ether, and the organic phases are combined and then dried over magnesium sulfate, filtered and evaporated. The crude product is chromatographed on a column of silica (eluting with a mixture of from 0% to 70% ethyl acetate in heptane). 2-tert-Butyl-7-methanesulfoximinobenzoxazole (0.57 g; 64%) is obtained.

MS (ES+) m/z 254 (MH+).

Example 9

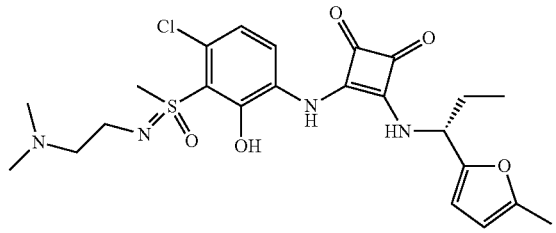

3-[4-Chloro-3-[N-(2-dimethylaminoethyl)-S-methylsulfonimidoyl]-2-hydroxyanilino]-4-ethoxycyclobut-3-ene-1,2-dione To a suspension of 3-[4-chloro-3-[4N-(2-dimethylaminoethyl)-S-methylsulfonimidoyl]-2-hydroxyanilino]-4-ethoxycyclobut-3-ene-1,2-dione (180 mg; 0.43 mmol) in methanol (7.20 ml) at room temperature are added (R)-1-(5-methylfuran-2-yl)propylane hydrochloride (91.23 mg; 0.52 mmol) and triethylamine (0.09 ml; 0.65 mmol). The reaction medium is heated at 60° C. for 2 hours. The reaction medium is concentrated and the crude product is chromatographed on silica gel (5-10% methanol in dichloromethane). 3-[4-Chloro-3-[N-(2-dimethylaminoethyl)-S-methylsulfonimidoyl]-2-hydroxyanilino]-4-ethoxy cyclobut-3-ene-1,2-dione (150 mg; 64%) is obtained. MS (ES+) m/z 510 (MH+).

1H NMR δ (ppm)(DMSO-$d_6$): 0.94-0.91 (3H, m), 1.85 (1H, dt, J=14.12, 7.12 Hz), 1.94 (1H, dd, J=13.35, 7.62 Hz), 2.26 (3H, d, J=4.16 Hz), 2.56 (3H, s), 2.85 (2H, br s), 2.90 (1H, s), 3.01 (1H, d, J=12.42 Hz), 3.22 (1H, d, J=14.18 Hz), 3.36 (3H, d, J=12.13 Hz), 5.16 (1H, d, J=8.68 Hz), 6.05 (1H, s), 6.24 (1H, d, J=10.88 Hz), 6.47 (1H, t, J=7.18 Hz), 7.99 (1H, dd, J=14.72, 8.42 Hz), 8.90 (1H, dd, J=30.8, 8.83 Hz), 9.40 (1H, s).

3-[4-Chloro-3-[N-(2-dimethylaminoethyl)-S-methylsulfonimidoyl]-2-hydroxyanilino]-4-ethoxycyclobut-3-ene-1,2-dione To a solution of 6-amino-3-chloro-2-[N-(2-dimethylaminoethyl)-S-methylsulfonimidoyl]phenol (190 mg; 0.65 mmol) in ethanol (5.70 ml) is added at room temperature 3,4-diethoxy-3-cyclobutene-1,2-dione (145 μl; 0.98 mmol). The reaction medium is heated at 60° C. for 2 hours. The ethanol is evaporated off and the residue is chromatographed on silica gel (5-10% methanol in dichloromethane). 3-[4-Chloro-3-[N-(2-dimethylaminoethyl)-S-methylsulfonimidoyl]-2-hydroxyanilino]-4-ethoxycyclobut-3-ene-1,2-dione (130 mg; 48%) is obtained. MS (ES+) m/z 418 (MH+).

6-Amino-3-chloro-2-[N-(2-dimethylaminoethyl)-S-methylsulfonimidoyl]phenol

To a solution of 2-[[(2-tert-butyl-6-chloro-1,3-benzoxazol-7-yl)methyloxosulfanylidene]amino]-N,N-dimethylethanamine (760 mg; 2.12 mmol) in 1,4-dioxane (11.40 ml) and water (3 ml) at room temperature is added, dropwise, concentrated sulfuric acid (2.1 ml; 39.11 mmol; 18.42 eq.). The reaction medium is stirred at 60° C. for 48 hours. The reaction medium is brought to pH=8 with 10M sodium hydroxide. The product is extracted 3 times with 25 ml of ethyl acetate. The organic phase is dried over magnesium sulfate and the solvents are then evaporated off. The residue obtained is chromatographed on a column of silica (2-10% methanol in dichloromethane). 6-Amino-3-chloro-2-[N-(2-dimethylaminoethyl)-S-methylsulfonimidoyl]phenol (280 mg; 45%) is obtained.

MS (ES+) m/z 292 (MH+).

2-[[(2-tert-Butyl-6-chloro-1,3-benzoxazol-7-yl)methyloxosulfanylidene]amino]-N,N-dimethylethanamine To a suspension of 2-tert-butyl-6-chlorobenzoxazole-7-sulfoximine (2.00 g; 6.97 mmol) in toluene (10 ml) is added at room temperature (triphenylphosphanylidene)acetonitrile (6.30 g; 20.92 mmol) and 2-dimethylaminoethanol (2.10 ml; 20.92 mmol). The medium is heated for 24 hours at 120° C. The reaction medium is partitioned between 25 ml of water and 25 ml of ethyl acetate. The aqueous phase is re-extracted once again with 25 ml of ethyl acetate. The organic phases are combined and then dried over magnesium sulfate, filtered and evaporated. The crude product is chromatographed on silica (2-10% methanol in dichloromethane). 2-[[(2-tert-Butyl-6-chloro-1,3-benzoxazol-7-yl)methyloxosulfanylidene]amino]-N,N-dimethylethanamine (1.00 g; 40%) is obtained. MS (ES+) m/z 359 (MH+).

Example 10

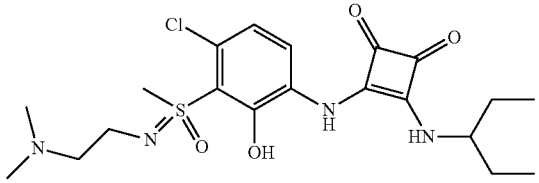 [SMILES: CCC(CC)Nc1c(Nc2ccc(Cl)c(S(C)(=O)=NCCN(C)C)c2O)c(=O)c1=O]

3-[4-Chloro-3-[N-(2-dimethylaminoethyl)-S-methylsulfonimidoyl]-2-hydroxyanilino]-4-(1-ethylpropylamino)cyclobut-3-ene-1,2-dione To a suspension of 3-[4-chloro-3-[N-(2-dimethylaminoethyl)-S-methylsulfonimidoyl]-2-hydroxyanilino]-4-ethoxycyclobut-3-ene-1,2-dione (80 mg; 0.19 mmol) in methanol (3.2 ml) is added at room temperature 1-ethylpropylamine (27 μl; 0.23 mmol). The reaction medium is heated at 60° C. for 48 hours. The reaction medium is concentrated and 100 mg of crude product are purified by preparative HPLC. 3-[4-Chloro-3-[N-(2-dimethylamino-ethyl)-S-methylsulfonimidoyl]-2-hydroxyanilino]-4-(1-ethylpropylamino)cyclobut-3-ene-1,2-dione (25 mg; 28%) is obtained.

1H NMR δ (ppm)(DMSO-d₆): 0.93-0.86 (6H, m), 1.52-1.42 (2H, m), 1.67-1.57 (2H, m), 2.55 (6H, s), 2.93-2.81 (2H, m), 3.04-2.97 (1H, m), 3.22 (1H, dt, J=13.96, 4.56 Hz), 3.37 (3H, s), 3.92-3.87 (1H, m), 6.47 (1H, d, J=8.43 Hz), 8.03 (1H, d, J=8.43 Hz), 8.43 (1H, d, J=9.05 Hz), 9.33 (1H, s). MS (ES+) m/z 457 (MH+).

Example 11

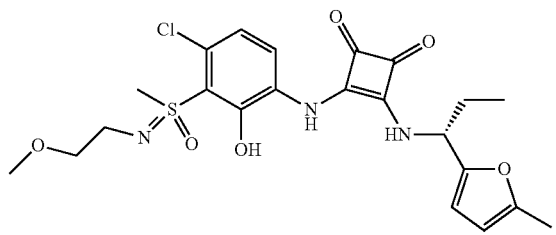

3-[4-Chloro-2-hydroxy-3-[N-(2-methoxyethyl)-S-methylsulfonimidoyl]anilino]-4-[[(1R)-1-(5-methyl-2-furyl)propyl]amino]cyclobut-3-ene-1,2-dione To a suspension of 3-[4-chloro-2-hydroxy-3-[N-(2-methoxyethyl)-S-methylsulfonimidoyl]anilino]-4-ethoxycyclobut-3-ene-1,2-dione (127 mg; 0.32 mmol) in methanol (5 ml) are added at room temperature (R)-1-(5-methylfuran-2-yl)propylane hydrochloride (66 mg; 0.38 mmol) and triethylamine (0.07 ml; 0.47 mmol). The reaction medium is heated at 50° C. for 2 hours and is then concentrated and the crude product is chromatographed on silica gel (eluent: 30-60% ethyl acetate in heptane). 3-[4-Chloro-2-hydroxy-3-[N-(2-methoxyethyl)-S-methylsulfonimidoyl]-anilino]-4-[[(1R)-1-(5-methyl-2-furyl)propyl]amino]cyclobut-3-ene-1,2-dione (85 mg; 54%) is obtained after treatment with diisopropyl ether. MS (ES+) m/z 496 (MH+).

1H NMR δ (ppm)(DMSO-d₆): 0.92 (3H, t, J=7.29 Hz), 1.89-1.84 (1H, m), 1.95 (1H, dd, J=13.89, 7.02 Hz), 2.27 (3H, s), 3.31 (3H, m), 3.46-3.39 (2H, m), 3.52 (2H, s), 3.68 (2H, s), 5.14 (1H, q, J=7.65 Hz), 6.06 (1H, s), 6.26 (1H, s), 7.01 (1H, s), 8.03 (1H, d, J=8.72 Hz), 8.78 (1H, d, J=8.82 Hz), 9.36 (1H, s).

3-[4-Chloro-2-hydroxy-3-[N-(2-methoxyethyl)-S-methylsulfonimidoyl]anilino]-4-ethoxycyclobut-3-ene-1,2-dione To a solution of 6-amino-3-chloro-2-methane[(N-2-methoxyethylamino)sulfoximino]phenol (0.50 g; 1.79 mmol) in ethanol (9.5 ml) is added at room temperature 3,4-diethoxy-3-cyclobutene-1,2-dione (0.40 ml; 2.69 mmol). The reaction medium is heated at 50° C. for 4 days. The medium is concentrated and the residue is chromatographed on silica gel (eluent: 2-5% methanol in dichloromethane). 3-[14-Chloro-2-hydroxy-3-[N-(2-methoxyethyl)-S-methylsulfonimidoyl]anilino]-4-ethoxycyclobut-3-ene-1,2-dione (127 mg; 17%) is obtained. MS (ES+) m/z 403 (MH+).

6-Amino-3-chloro-2-methane[(N-2-methoxyethyl-amino)sulfoximino]phenol

To a solution of 2-tert-butyl-6-chloro-7-methane-N-(2-methoxyethylamino)sulfoximinobenzoxazole (0.70 g; 2.03 mmol) in 1,4-dioxane (4.9 ml) and water (1.12 ml) is added dropwise at room temperature concentrated sulfuric acid (0.84 ml; 15.72 mmol). The reaction medium is heated at 110° C. for 4 hours. The reaction medium is concentrated and 28 ml of 1N sodium hydroxide are added (to pH 7), followed by extraction with 50 ml of ethyl acetate. The organic phase is dried over magnesium sulfate and filtered, and the solvents are evaporated off 6-Amino-3-chloro-2-methane[(N-2-methoxyethylamino)sulfoximino]phenol (0.40 g; 70%) is obtained. MS (ES+) m/z 279 (MH+).

2-tert-Butyl-6-chloro-7-methane-N-(2-methoxyethylamino)sulfoximinobenzoxazole

To a solution of 2-tert-butyl-6-chlorobenzoxazole-7-sulfoximine (1.00 g; 3.49 mmol) in N,N-dimethylformamide (15 ml) is added at room temperature sodium hydride at 60% in oil (0.21 g; 5.23 mmol). The medium is stirred for 10 minutes at room temperature and 2-bromoethyl methyl ether (0.49 ml; 5.23 mmol) is then added. The reaction medium is stirred at room temperature for 24 hours. Further sodium hydride at 60% in oil (21 mg; 0.52 mmol) and 2-bromoethyl methyl ether (0.07 ml; 0.70 mmol) are added to the reaction medium, and the medium is stirred for 2 hours at 60° C. The reaction medium is partitioned between 30 ml of water and 30 ml of ethyl acetate, and the organic phase is washed 3 times with 20 ml of water and then dried over magnesium sulfate, filtered and evaporated. The residue is chromatographed on silica gel (eluent: 30-50% ethyl acetate in heptane). 2-tert-Butyl-6-chloro-7-methane-N-(2-methoxyethylamino)sulfoximinobenzoxazole (0.70 g; 58%) is obtained. MS (ES+) m/z 345 (MH+).

Example 12

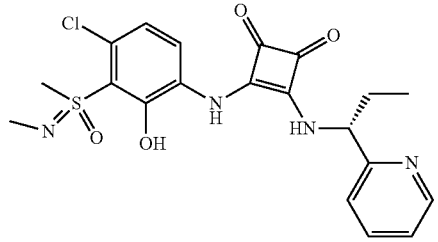 [SMILES: CC[C@@H](Nc1c(Nc2ccc(Cl)c(S(C)(=O)=NC)c2O)c(=O)c1=O)c1ccccn1]

(−)-3-{4-Chloro-2-hydroxy-3-methane[(N-methyl)sulfoximino]phenylamino}-4-[(R)-1-(pyridin-2-yl)propylamino]cyclobut-3-ene-1,2-dione A mixture of (−)-3-(4-chloro-2-hydroxy-3-methane[(N-methyl)sulfoximino]phenylamino)-4-ethoxycyclobut-3-ene-1,2-dione (216 mg; 0.60 mmol; prepared from enantiomer A, (−)-2-tert-butyl-6-chloro-7-methanesulfoximinobenzoxazole) and (R)-1-pyridin-2-ylpropylamine hydrochloride (125 mg; 0.72 mmol) in methanol (5 ml) and in the presence of triethylamine (100 μl; 0.72 mmol) is heated at 50° C. for 7 hours and stirred at room temperature for 16 hours. The solvent is evaporated off and the residue is chromatographed on HP silica gel (puriFlash PF-15HP/25 g, CombiFlash column) eluted with dichloromethane/ethyl acetate (90/10 to 70/30). The solid is taken up in a small amount of ethyl acetate, filtered and dried under vacuum at 45° C. (−)-3-{4-Chloro-2-hydroxy-3-methane[(N-methyl) sulfoximino]phenylamino}-4-[(R)-1-(pyridin-2-yl)propylamino]cyclobut-3-ene-1,2-dione (156 mg; 57%) is obtained. MS (ES+) m/z 449 (MH+); t=5.37 min; 100%; [α]$_D$=−32.3° (c=10 mg/ml; ethanol).

1H NMR (400 MHz, DMSO-d$_6$): δ (ppm) 0.85-0.89 (t, J=7.3 Hz, 3H), 1.84-1.97 (m, 2H), 2.91 (s, 3H), 3.69 (s, 3H), 5.23-5.29 (q, J=7.4 Hz, 1H), 6.98 (d, J=8.7 Hz, 1H), 7.34-7.37 (m, 1H), 7.41 (d, J=7.8 Hz, 1H), 7.81-7.85 (td, J=7.7-1.6 Hz, 1H), 8.01 (d, J=8.7 Hz, 1H), 8.63 (d, J=4.4 Hz, 1H), 9.05-9.08 (d, J=9.1 Hz, 1H).

Example 13

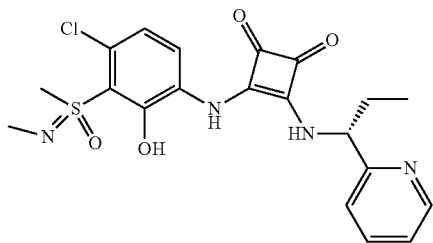 [SMILES: CC[C@@H](Nc1c(Nc2ccc(Cl)c(S(C)(=O)=NC)c2O)c(=O)c1=O)c1ccccn1]

(+)-3-{4-Chloro-2-hydroxy-3-methane[(N-methyl) sulfoximino]phenylamino}-4-[(R)-1-(pyridin-2-yl) propylamino]cyclobut-3-ene-1,2-dione A mixture of (+)-3-(4-chloro-2-hydroxy-3-methane[(N-methyl)sulfoximino]-phenylamino)-4-ethoxycyclobut-3-ene-1,2-dione (76 mg; 0.21 mmol; prepared from enantiomer B, (+)-2-tert-butyl-6-chloro-7-methanesulfoximinobenzoxazole) and (R)-1-pyridin-2-ylpropylamine hydrochloride (44 mg; 0.25 mmol) in methanol (1.50 ml) and in the presence of triethylamine (0.04 ml; 0.25 mmol) is heated at 50° C. for 7 hours and stirred at room temperature for 16 hours. The solvent is evaporated off and the residue is chromatographed on HP silica gel (puriFlash PF-15HP/4G, CombiFlash column) eluted with dichloromethane/ethyl acetate (90/10 to 70/30). The solid is taken up in a small amount of heptane/ethyl acetate, filtered off and dried under vacuum at 45° C. (+)-3-{4-Chloro-2-hydroxy-3-methane[(N-methyl)sulfoximino]phenylamino}-4-[(R)-1-(pyridin-2-yl)propylamino]cyclobut-3-ene-1,2-dione (41 mg; 42%) is obtained; MS (ES+) m/z 449 (MH+); t=5.34 min, 98.6%.

1H NMR (400 MHz, DMSO-d$_6$): δ (ppm) 0.85-0.89 (t, J=7.3 Hz, 3H), 1.84-1.99 (m, 2H), 2.91 (s, 3H), 3.69 (s, 3H), 5.23-5.29 (q, J=7.4 Hz, 1H), 6.98 (d, J=8.7 Hz, 1H), 7.34-7.37 (m, 1H), 7.41 (d, J=7.8 Hz, 1H), 7.81-7.85 (td, J=7.7-1.6 Hz, 1H), 8.01 (d, J=8.7 Hz, 1H), 8.63 (d, J=4.4 Hz, 1H), 9.05-9.08 (d, J=9.1 Hz, 1H).

Example 14

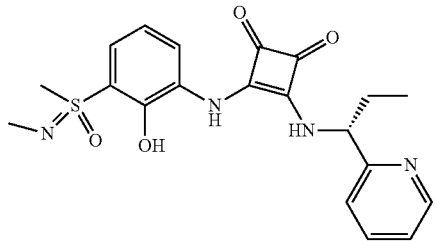 [SMILES: CC[C@@H](Nc1c(Nc2cccc(S(C)(=O)=NC)c2O)c(=O)c1=O)c1ccccn1]

(−)-3-{12-Hydroxy-3-methane[(N-methyl)sulfoximino]phenylamino}-4-[(R)-1-(pyridin-2-yl)propylamino]cyclobut-3-ene-1,2-dione A mixture of (−)-3-(2-hydroxy-3-methane[(N-methyl)sulfoximino]phenylamino)-4-ethoxycyclobut-3-ene-1,2-dione (586 mg; 1.81 mmol; prepared from enantiomer A, (−)-2-tert-butyl-6-chloro-7-methanesulfoximinobenzoxazole) and (R)-1-pyridin-2-ylpropylamine hydrochloride (374 mg; 2.17 mmol) in methanol (10 ml) and in the presence of triethylamine (300 μl; 2.17 mmol) is heated at 50° C. for 2 days. The solvent is evaporated off and the residue is chromatographed on HP silica gel (puriFlash PF-15HP/40G, CombiFlash column) eluted with dichloromethane/methanol (98/2 to 95/5). The solid is taken up in a small amount of heptane/ethyl acetate, filtered off and dried under vacuum at 45° C. (−)-3-{2-Hydroxy-3-methane[(N-methyl)sulfoximino]phenylamino}-4-[(R)-1-(pyridin-2-yl)propylamino]cyclobut-3-ene-1,2-dione (175 mg; 23%) is obtained; MS (ES+) m/z 415 (MH+); 1=4.29 min; 98.51%; [α]$_D$=−69.4° (c=8.5 mg/ml).

1H NMR (400 MHz, DMSO-d$_6$): δ (ppm) 0.86-0.89 (t, J=7.3 Hz, 3H), 1.83-1.98 (m, 2H), 2.83 (s, 3H), 3.44 (s, 3H), 5.24-5.30 (q, J=7.3 Hz, 1H), 6.88-6.92 (t, J=8.1 Hz, 1H), 7.34-7.39 (m, 1H), 7.41-7.43 (t, J=6.2 Hz, 1H), 7.81-7.86 (td, J=7.7-1.6 Hz, 1H), 8.0-8.02 (d, J=8.8 Hz, 1H), 8.63-8.64 (d, J=4.2 Hz, 1H), 9.0-9.02 (d, J=9.2 Hz, 1H).

Example 15

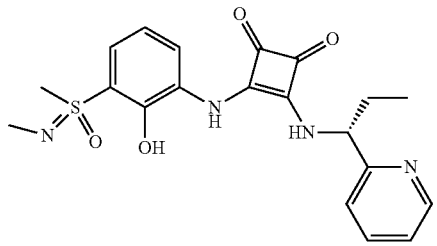 [SMILES: CC[C@@H](Nc1c(Nc2cccc(S(C)(=O)=NC)c2O)c(=O)c1=O)c1ccccn1]

(−)-3-{12-Hydroxy-3-methane[(N-methyl)sulfoximino]phenylamino}-4-[(R)-1-(pyridin-2-yl)propylamino]cyclobut-3-ene-1,2-dione A mixture of (+)-3-(2-hydroxy-3-methane[(N-methyl)sulfoximino]phenylamino)-4-ethoxycyclobut-3-ene-1,2-dione (150 mg; 0.46 mmol; prepared from enantiomer B, (+)-2-tert-butyl-6-chloro-7-methanesulfoximinobenzoxazole) and (R)-1-pyridin-2-ylpropylamine hydrochloride (96 mg; 0.55 mmol) in methanol (4 ml) and in the presence of triethylamine (77 µl; 0.55 mmol) is heated at 50° C. for 14 hours and then at 55° C. for 2 days. The solvent is evaporated off and the residue is chromatographed on silica gel as a solid deposit (puriFlash IR-50SI/12G, CombiFlash column) eluted with dichloromethane/methanol (98/2 to 95/5). The solid is taken up in a small amount of heptane/ethyl acetate, filtered off and dried under vacuum at 45° C. (−)-3-{2-Hydroxy-3-methane[(N-methyl)sulfoximino]phenylamino}-4-[(R)-1-(pyridin-2-yl)propylamino]cyclobut-3-ene-1,2-dione (158 mg; 81%) is obtained; MS (ES+) m/z 415 (MH+); t=0.92 min; [414]; [α]$_D$=−5.2° (c=10.1 mg/ml).

1H NMR (400 MHz, DMSO-d$_6$): δ (ppm) 0.85-0.89 (t, J=7.3 Hz, 3H), 1.83-1.99 (m, 2H), 2.83 (s, 3H), 3.45 (s, 3H), 5.24-5.30 (q, J=7.3 Hz, 1H), 6.88-6.92 (t, J=8.1 Hz, 1H), 7.34-7.39 (m, 1H), 7.41-7.43 (t, J=6.2 Hz, 1H), 7.81-7.86 (td, J=7.7-1.6 Hz, 1H), 8.0-8.02 (d, J=8.8 Hz, 1H), 8.63-8.64 (d, J=4.2 Hz, 1H), 9.0-9.02 (d, J=9.2 Hz, 1H).

Example 16

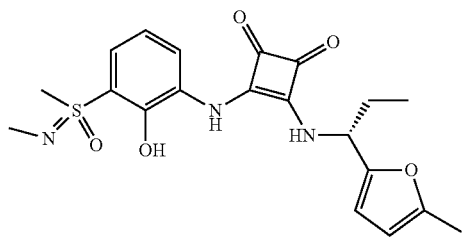

(+)-3-{2-Hydroxy-3-methane[(N-methyl)sulfoximino]phenylamino}-4-[(R)-1-(5-methylfuran-2-yl)propylamino]cyclobut-3-ene-1,2-dione A mixture of (−)-3-(2-hydroxy-3-methane[(N-methyl)sulfoximino]phenylamino)-4-ethoxycyclobut-3-ene-1,2-dione (586 mg; 1.81 mmol; prepared from enantiomer A, (−)-2-tert-butyl-6-chloro-7-methanesulfoximinobenzoxazole) and (R)-1-(5-methylfuran-2-yl)propylane hydrochloride (381 mg; 2.17 mmol) in methanol (10 ml) and in the presence of triethylamine (301 µl; 2.17 mmol) is heated at 50° C. for 15 hours. The solvent is evaporated off and the residue is chromatographed on HP silica gel (puriFlash PF-15HP/40G, CombiFlash column) eluted with dichloromethane/methanol (98/2 to 95/5). The solid is taken up in a small amount of heptane/ethyl acetate, filtered off and dried under vacuum at 45° C. (+)-3-{12-Hydroxy-3-methane[(N-methyl)sulfoximino]phenylamino}-4-[(R)-1-(5-methylfuran-2-yl)propylamino]cyclobut-3-ene-1,2-dione (751 mg; 98%) is obtained; MS (ES+) m/z 418 (MH+); 1=5.97 min; 99.19%; [α]$_D$=+22.0° (c=10.2 mg/ml).

1H NMR (400 MHz, DMSO-d$_6$): δ (ppm) 0.90-0.94 (t, J=7.3 Hz, 3H), 1.80-1.89 (m, 1H), 1.91-1.99 (m, 1H), 2.27 (s, 3H), 2.82 (s, 3H), 3.45 (s, 3H), 5.10-5.16 (q, J=7.7 Hz, 1H), 6.05 (dd, J=1.0 Hz, 1H), 6.26 (d, J=3.0 Hz, 1H), 6.88-6.92 (t, J=8.0 Hz, 1H), 7.39-7.41 (d, J=8.1 Hz, 1H), 8.03-8.05 (d, J=7.8 Hz, 1H), 8.70-8.72 (d, J=9.0 Hz, 1H), 9.36 (s, 1H).

MS (ES+) m/z 418 (MH+).

Example 17

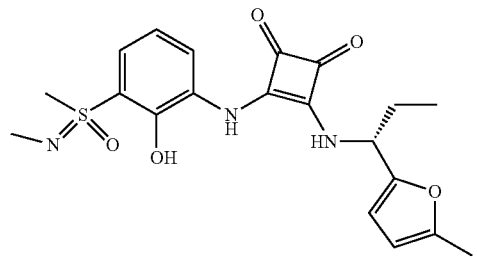

(+)-3-{2-Hydroxy-3-methane[(N-methyl)sulfoximino]phenylamino}-4-[(R)-1-(5-methylfuran-2-yl) propylamino]cyclobut-3-ene-1,2-dione A mixture of (+)-3-(2-hydroxy-3-methane[(N-methyl)sulfoximino]phenylamino)-4-ethoxycyclobut-3-ene-1,2-dione (150 mg; 0.46 mmol; prepared from enantiomer B, (+)-2-tert-butyl-6-chloro-7-methanesulfoximinobenzoxazole) and (R)-1-(5-methylfuran-2-yl)propylane hydrochloride (97 mg; 0.55 mmol) in methanol (4 ml) and in the presence of triethylamine (77 µl; 0.55 mmol) is heated at 50° C. for 12 hours. The solvent is evaporated off and the residue is chromatographed on silica gel as a solid deposit (puriFlash IR-50SI/12G, CombiFlash column) eluted with dichloromethane/methanol (98/2 to 95/5). The solid is taken up in a small amount of heptane/ethyl acetate, filtered off and dried under vacuum at 45° C. (+)-3-{2-Hydroxy-3-methane[(N-methyl)sulfoximino]phenylamino}-4-[(R)-1-(5-methylfuran-2-yl)propylamino]cyclobut-3-ene-1,2-dione (158 mg; 81%) is obtained; MS (ES+) m/z 418 (MH+); 1=5.98 min; 99.66%; [α]$_D$=+94.1° (c=10.1 mg/ml).

1H NMR (400 MHz, DMSO-d$_6$): δ (ppm) 0.90-0.94 (t, J=7.3 Hz, 3H), 1.80-1.89 (m, 1H), 1.91-1.99 (m, 1H), 2.27 (s, 3H), 2.82 (s, 3H), 3.45 (s, 3H), 5.10-5.16 (q, J=7.7 Hz, 1H), 6.05 (dd, J=1.0 Hz, 1H), 6.26 (d, J=3.0 Hz, 1H), 6.88-6.92 (t, J=8.0 Hz, 1H), 7.38-7.41 (dd, J=8.2-1.4 Hz, 1H), 8.03-8.05 (d, J=7.8 Hz, 1H), 8.70-8.73 (d, J=9.0 Hz, 1H), 9.35 (s, 1H).

Example 18

(−)-3-(2-Hydroxy-3-methane[(N-methyl)sulfoxim] phenylamino[4-(1-ethylpropylamino]cyclobut-3-ene-1,2-dione A mixture of (−)-3-(2-hydroxy-3-methane[(N-methyl)sulfoximino]phenylamino)-4-ethoxycyclobut-3-ene-1,2-dione (586 mg; 1.81 mmol), prepared from enantiomer A, (−)-2- tert-butyl-6-chloro-7-methanesulfoximinobenzoxazole), and 1-ethylpropylamine (0.25 ml; 2.17 mmol) in methanol (10 ml) is heated at 50° C. for 15 hours. The solvent is evaporated off and the residue is chromatographed on HP silica gel (puriFlash PF-15HP/40G, CombiFlash column) eluted with dichloromethane/methanol (98/2 to 95/5). The solid is taken up in a small amount of heptane/ethyl acetate, filtered off and dried under vacuum at 45° C. (−)-3-(2-Hydroxy-3-methane[(N-methyl) sulfoxim]phenylamino[4-(1-ethylpropylamino]cyclobut-3-ene-1,2-dione (584 mg; 88%) is obtained in the form of a pale yellow solid; MS (ES−) m/z 364 (MH−); t=5.20 min; 99.57%; [α]$_D$=−45.8° (c=10.0 mg/ml).

1H NMR (400 MHz, DMSO-d$_6$): δ (ppm) 0.86-0.90 (t, J=7.4 Hz, 3H), 0.88-0.92 (t, J=7.3 Hz, 3H), 1.42-1.53 (m, 2H), 1.58-1.68 (m, 2H), 2.83 (s, 3H), 3.46 (s, 3H), 3.85-3.94 (m, 1H), 6.88-6.92 (t, J=8.0 Hz, 1H), 7.37-7.40 (dd, J=8.7 Hz, 1H), 8.07-8.09 (d, J=8.1-1.0 Hz, 1H), 8.06-8.08 (d, J=7.2 Hz, 1H), 8.23-8.25 (d, J=9.0 Hz, 1H), 9.30 (s, 1H).

Example 19

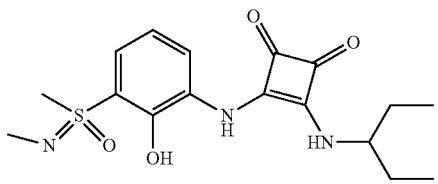 [SMILES: CCC(CC)Nc1c(Nc2cccc(S(C)(=O)=NC)c2O)c(=O)c1=O]

(+)-3-(2-Hydroxy-3-methane[(N-methyl)sulfoxim] phenylamino[4-(1-ethylpropylamino]cyclobut-3-ene-1,2-dione A mixture of (+)-3-(2-hydroxy-3-methane[(N-methyl)sulfoximino]phenylamino)-4-ethoxycyclobut-3-ene-1,2-dione (150 mg; 0.46 mmol; prepared from enantiomer B, (+)-2-tert-butyl-6-chloro-7-methanesulfoximinobenzoxazole and 1-ethylpropylamine (65 μl; 0.55 mmol) in methanol (4 ml) is heated at 50° C. for 12 hours. The solvent is evaporated off and the residue is chromatographed on silica gel as a solid deposit (puriFlash IR-50SI/12G, CombiFlash column) eluted with dichloromethane/methanol (98/2 to 95/5). The solid is taken up in a small amount of heptane/ethyl acetate, filtered off and dried under vacuum at 45° C. (+)-3-(2-Hydroxy-3-methane[(N-methyl)sulfoxim]phenylamino[4-(1-ethylpropylamino]cyclobut-3-ene-1,2-dione (156 mg; 91%) is obtained; MS (ES+) m/z 366 (MH+); t=5.22 min; 99.26%; [α]$_D$=+40.8° (c=10.2 mg/ml).

1H NMR (400 MHz, DMSO-d$_6$): δ (ppm) 0.86-0.90 (t, J=7.4 Hz, 3H), 0.88-0.92 (t, J=7.3 Hz, 3H), 1.42-1.53 (m, 2H), 1.58-1.68 (m, 2H), 2.83 (s, 3H), 3.46 (s, 3H), 3.85-3.94 (m, 1H), 6.88-6.92 (t, J=8.0 Hz, 1H), 7.37-7.40 (dd, J=8.1-1.2 Hz, 1H), 8.07-8.09 (d, J=8.1-1.0 Hz, 1H), 8.06-8.08 (d, J=7.2 Hz, 1H), 8.23-8.25 (d, J=9.0 Hz, 1H), 9.30 (s, 1H).

Example 20

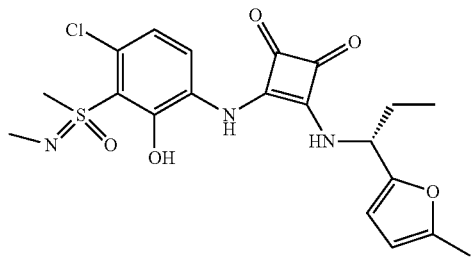

(+)-3-{4-Chloro-2-hydroxy-3-methane[(N-methyl) sulfoximino]phenylamino}-4-[(R)-1-(5-methylfuran-2-yl)propylamino]cyclobut-3-ene-1,2-dione A mixture of (−)-3-(4-chloro-2-hydroxy-3-methane[(N-methyl)sulfoximino]-phenylamino)-4-ethoxycyclobut-3-ene-1,2-dione (270 mg; 0.75 mmol), prepared from enantiomer A, (−)-2-tert-butyl-6-chloro-7-methanesulfoximinobenzoxazole), and (R)-1-(5-methylfuran-2-yl)propylane hydrochloride (158.6 mg; 0.90 mmol) in methanol (5 ml) and in the presence of triethylamine (125 μl; 0.90 mmol) is heated at 50° C. for 38 hours. The solvent is evaporated off and the residue is chromatographed on HP silica gel (puriFlash PF-15HP/25 g, CombiFlash column) eluted with dichloromethane/ethyl acetate (95/5 to 90/10). The solid is taken up in a small amount of heptane/ethyl acetate, filtered off and dried under vacuum at 45° C. (−)-3-{4-Chloro-2-hydroxy-3-methane[(N-methyl)sulfoximino]phenylamino}-4-[(R)-1-(5-methylfuran-2-yl)propylamino]cyclobut-3-ene-1,2-dione (228 mg; 65%) is obtained in the form of a pale yellow solid; 1=17.1 min; 99.6%; [α]$_D$=+30.8° (c=2.5 mg/ml).

1H NMR (400 MHz, DMSO-d$_6$): δ (ppm) 0.90-0.94 (t, J=7.3 Hz, 3H), 1.82-1.99 (m, 2H), 2.27 (s, 3H), 2.90 (s, 3H), 3.69 (s, 3H), 5.10-5.16 (q, J=7.7 Hz, 1H), 6.06 (dd, J=1.0 Hz, 1H), 6.26 (d, J=3.0 Hz, 1H), 6.97-6.99 (d, J=8.7 Hz, 1H), 8.03-8.05 (d, J=8.7 Hz, 1H), 8.75-8.77 (d, J=9.0 Hz, 1H), 9.35 (s, 1H).

Biological Tests

Example 21: In Vitro Affinity

The in vitro affinity of the compounds of the present invention for the CXCR1 and CXCR2 receptors is determined on a functional test of β-arrestin recruitment type after activation of the receptor.

It has been demonstrated that activation by CXCL8 of the CXCR2 receptor in cells of the PathHunter HEK293-CXCR2 line or of the CXCR1 receptor in cells of the U2OS h CXCR1 β-arrestin line leads to the recruitment of β-arrestin (Richardson, R. M., R. J. Marjoram, L. S. Barak, R. Snyderman. 2003. Role of the cytoplasmic tails of CXCR1 and CXCR2 in mediating leukocyte migration, activation, and regulation. J. Immunol. 170: 2904-2911).

To evaluate the direct interaction of the CXCR2 or CXCR1 receptor with β-arrestin 2, a test of β-arrestin 2 recruitment for CXCR2 or CXCR1 based on complementation of the β-galactosidase enzyme (Olson K. R., Eglen R. M., Beta-galactosidase complementation: a cell-based luminescent assay platform for drug discovery. Assay Drug Dev. Technol. 2007 February; 5(1); 137-44), as established by DiscoveRx Corporation was used. Stimulation of these two cell lines with CXCL8 (10 nM) induces the recruitment of β-arrestin 2, as indicated by a significant increase in the induction factor. All the CXCR2 antagonists are tested in a dose-dependent manner and the concentration corresponding to 50% inhibition of the response is determined ($IC_{50}$=concentration of half-inhibition).

β-Arrestin Recruitment Test: "PathHunter HEK293-CXCR2" or "U2OS hCXCR1 β-arrestin" cells (DiscoveRx Corporation) were seeded overnight at 10 000 cells/well (384-well format) in 20 μl of Opti MEM I medium. Preincubation with the antagonist or the vehicle for 30 minutes at 37° C. and 5% CO2 was followed by 60 minutes of stimulation with CXCL8 at 37° C. and 5% CO2. The cells were then placed at room temperature for 30 minutes. The PathHunter detection reagent (DiscoveRx Corporation) was added. After incubation for 60 minutes at room temperature, the β-galactosidase induced by the luminescence during the β-arrestin-CXCR2 interaction was measured for 0.3 s in an Envision 2102 Multilabel Reader (PerkinElmer Life and Analytical Sciences). The data are analysed via a non-linear curve procedure using the XLFit4 (IDBS) exploitation software, and the $IC_{50}$ values are determined.

TABLE 3

| Example No. | CXCR2 IC50 (nM) | CXCR1 IC50 (nM) |
|---|---|---|
| 1 | A | C |
| 2 | A | C |
| 3 | B | D |
| 4 | B | D |
| 5 | B | C |
| 6 | B | D |
| 7 | B | D |
| 8 | B | C |
| 9 | B | D |
| 10 | B | D |
| 11 | B | D |
| 12 | A | C |
| 13 | B | D |
| 14 | B | C |
| 15 | B | D |
| 16 | A | C |
| 17 | B | D |
| 18 | B | D |
| 19 | B | D |
| 20 | A | C |

A: $IC_{50}$ < 20 nM;
B: $IC_{50}$ ≥ 20 nM
C: $IC_{50}$ < 200 nM;
D: $IC_{50}$ ≥ 200 nM

Example 22: Neutrophil Migration

Purification and Culturing of Human Neutrophils

Peripheral blood preparations (18-24 hours) are collected in duly registered clinics or clinical laboratories from healthy volunteers who consented to the re-use of their blood for scientific research (Supplier: Biopredic International). The neutrophils are separated from the whole blood via a positive selection (Whole Blood CD15 MicroBeads: MiltenyiBiotech, Reference: 130-091-058). The cells are resuspended at a rate of $4 \times 10^6$ cells per mL in RPMI 1640 culture medium (Invitrogen) supplemented with filtered and heat-inactivated 5% foetal calf serum (FCS) (Invitrogen).

Chemotaxis Assay

The experiments were performed in "HTS Transwell 96 Well Permeable Supports 3-μm pore size" filter plates (Corning, Reference: 3386). The response doses of CXCRS antagonists are applied in the lower compartments of the plates in the presence of 10 nM of IL-8 (1-72 aa, R&D Systems, Cat. No. IL-208). The neutrophils are then seeded in the upper compartment ($2 \times 10^5$ cells/well). After 1 hour of incubation at 37° C. and 5% CO2, the number of viable cells that have crossed the membrane and are in the lower compartment is determined via a colorimetric method (Cell-Titer 96® $AQ_{ueous}$ One Solution Cell Proliferation Assay PROMEGA Cat#G3581). Each treatment condition is evaluated in duplicate. The $IC_{50}$ values are calculated with the XLFit4 software.

TABLE 4

| Example No. | Migration of human neutrophils IC50 (nM) |
|---|---|
| 1 | E |
| 2 | E |
| 3 | ND |
| 4 | ND |
| 5 | E |
| 6 | ND |
| 7 | ND |
| 8 | F |
| 9 | ND |
| 10 | ND |
| 11 | ND |
| 12 | E |
| 13 | ND |
| 14 | F |
| 15 | ND |
| 16 | F |
| 17 | ND |
| 18 | F |
| 19 | ND |
| 20 | E |

ND: not determined;
E: $IC_{50}$ < 300 nM;
F: $IC_{50}$ ≥ 300 nM

The invention claimed is:
1. A compound corresponding to the general formula (I) below, or a salt thereof or an enantiomer thereof:

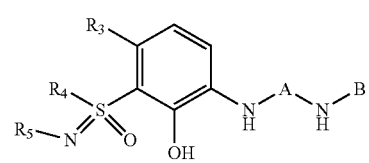

in which:
A represents

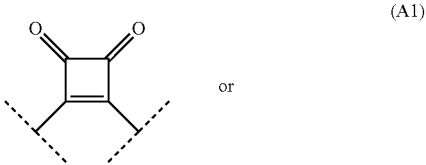

or

B represents

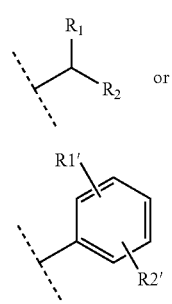
(B1)

or (B2)

with
- R1' and R2', which are identical or different, represent a hydrogen, a halogen, a C1 to C5 alkyl which is unsubstituted or substituted with one or more fluorine atoms, a C1 to C5 alkoxy, OCF3, OH, CN or NR11R12,
- R1 and R2, which are identical or different, represent:
  - a hydrogen,
  - a C1 to C5 alkyl, which is unsubstituted or substituted with one or more groups selected from the group consisting of F, OH, OCH3 and NR11R12; R11 and R12 having the meaning given below, it being understood that when the C1 to C5 alkyl radical is substituted only with one or more fluorine atoms, it is a C1 to C5 fluoroalkyl radical or perfluoroalkyl radical,
  - a C1 to C5 alkyl in which a carbon atom is replaced with an oxygen atom or with a sulfur atom, said C1 to C5 alkyl being unsubstituted or substituted with one or more groups selected from the group consisting of F, OH and NR11R12, R11 and R12 having the meaning given below,
  - a C3 to C8 cycloalkyl radical,
  - a C2 to C5 alkyne, which is unsubstituted or substituted with one or more groups selected from the group consisting of F, OH, phenyl and NR11R12, R11 and R12 having the meaning given below,
  - a cycloalkyl corresponding to one of the formulae (1), (2), (3), (4), (5) or (6) below in which R5', X and X' have the meanings given below:

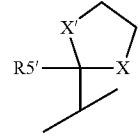
(1)

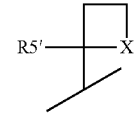
(2)

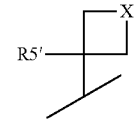
(3)

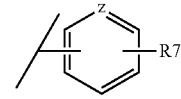
(4)

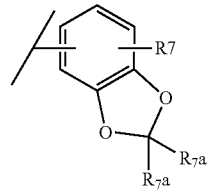
(5)

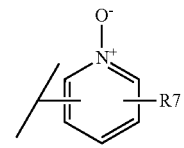
(6)

an aromatic or heteroaromatic ring selected from the group consisting the rings corresponding to formulae (a) to (o) below in which R7, R7a, Y and have the meanings given below:

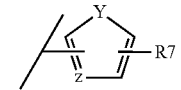
(a)

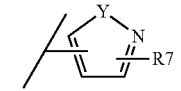
(b)

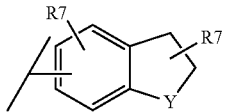
(c)

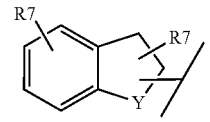
(d)

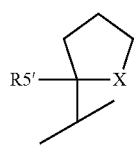
(e)

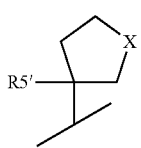
(f)

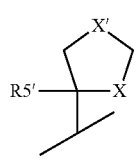
(g)

-continued

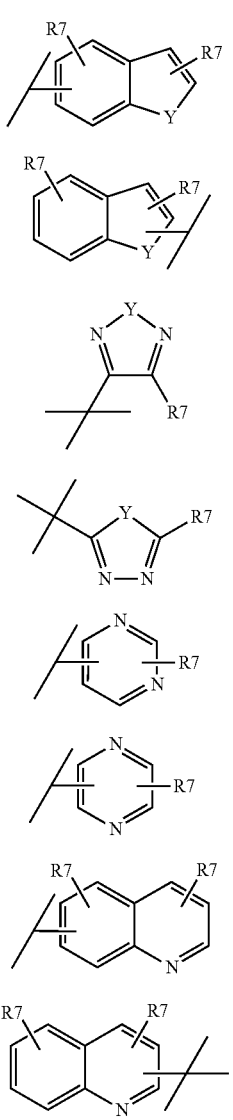

R7 can be present several times on a ring, and at most as many times as there are substitutable atoms; the meanings of each substituent R7 are identical or different, R3 represents a hydrogen, a halogen, a C1 to C5 alkyl, a C1 to C5 alkoxy, —CF3, —OCF3, —OH, —NO2 or CN, R4 and R5, which are identical or different, represent:
a hydrogen,
a C1 to C8 alkyl, which is unsubstituted or substituted with one or more groups selected from the group consisting of F, OH and NR11R12, R11 and R12 having the meaning given below,
a C1 to C8 alkyl in which a carbon atom is replaced with a nitrogen atom, with an oxygen atom or with a sulfur atom, said C1 to C8 alkyl being unsubstituted or substituted with one or more groups selected from the group consisting of F, OH and NR11R12, R11 and R12 having the meaning given below,
a C3 to C8 cycloalkyl radical,
a C3 to C8 cycloalkyl radical, one of the carbon atoms of which is replaced with an oxygen atom or with a nitrogen atom substituted with a radical R7a,
a heterocycloalkyl of 5 to 7 ring atoms,
a cycloalkylalkyl, the cycloalkyl being C3 to C8 and the alkyl C1 to C8,
a phenyl,
a phenyl substituted with a radical R7,
a heteroaryl,
an arylalkyl, the alkyl being C1-05,
a heteroarylalkyl, the alkyl being C1-05,
or alternatively R4 and R5 represent a chain —(CH$_2$)$_m$— forming a ring containing from 5 to 8 atoms with the sulfur and nitrogen atoms to which they are respectively attached, one of the carbons of the ring being optionally replaced with an oxygen or sulfur atom or with a nitrogen atom substituted with a radical R8; m and R8 having the meanings given below, R5' represents a hydrogen atom, a fluorine, an alkyl radical comprising from 1 to 5 carbon atoms inclusive or a fluoroalkyl or perfluoroalkyl radical comprising from 1 to 5 carbon atoms, R6 represents a hydrogen atom, a radical —COOtBu or a radical —COOBn, R7 represents a hydrogen, a C1 to C3 alkyl, a halogen, —CF3, —COR9, —OR9, —NR9R10, —NO2, —CN, —SO2R9, —S(O)R9, —S(=O)(=NR9)R10', —SO2NR9R10, —NR9SO2R10, —NR9COR10, —NR9CO2R10, —CONR9R10 or —CO2R9, R7a represents a hydrogen or a C1 to C5 alkyl, R8 represents a hydrogen, —OH, —SO2R9, —COR9, —CO2R9, an aryl, a heteroaryl, an arylalkyl, a heteroarylalkyl, an alkyl, a cycloalkyl or alternatively a cycloalkylalkyl, R9 and R10 are identical or different and are selected from the group consisting of a hydrogen, an aryl, a heteroaryl, an arylalkyl, a heteroarylalkyl, an alkyl, a cycloalkyl and a cycloalkylalkyl, or alternatively R9 and R10 can be linked together when they are borne by the same nitrogen atom so as to form a 3- to 7-membered heterocycle comprising one or two heteroatoms chosen from oxygen, sulfur and nitrogen in addition to the nitrogen atom to which they are attached, R10' represents an aryl, a heteroaryl, an arylalkyl, a heteroarylalkyl, an alkyl, a cycloalkyl or a cycloalkylalkyl, R11 and R12, which are identical or different, represent a hydrogen, a C1 to C5 alkyl, a C3 to C6 cycloalkyl, or a chain —(CH$_2$)$_p$— forming a ring containing from 4 to 6 atoms with the nitrogen atom to which they are attached, X and X', which are identical or different, represent an oxygen atom, a sulfur atom or a nitrogen atom substituted with a radical R6, Y represents an oxygen atom, a sulfur atom or a nitrogen atom substituted with a radical R8, Z represents a carbon atom or a nitrogen atom, m=3, 4, 5 or 6 and p=3, 4 or 5.

2. The compound according to claim 1, wherein in the abovementioned formula (I):

A represents

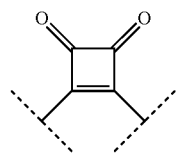
(A1)

B represents

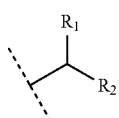
(B1)

R1 represents a hydrogen, a C1 to C5 alkyl, a C3 to C8 cycloalkyl radical, or a cycloalkyl corresponding to formula (1') below in which X has the meaning given below:

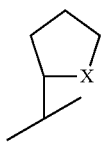
(1')

R2 represents:
- a C1 to C5 alkyl, which is unsubstituted or substituted with one or more groups chosen from F, it being understood that when the C1 to C5 alkyl radical is substituted only with one or more fluorine atoms, it is a C1 to C5 fluoroalkyl radical or perfluoroalkyl radical,
- a C1 to C5 alkyl in which a carbon atom is replaced with an oxygen atom,
- a C2 to C5 alkyne, which is unsubstituted or substituted with one or more groups chosen from fluorine and phenyl,
- an aromatic or heteroaromatic ring selected from the group consisting of the rings corresponding to formulae (a), (b1) and (d1) below in which R7 and Z have the meanings given below:

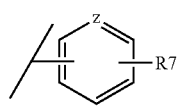
(a)

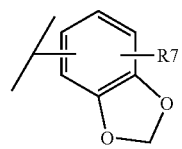
(b1)

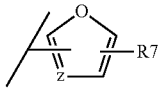
(d1)

R7 can be present several times on a ring, and at most as many times as there are substitutable atoms; the meanings of each substituent R7 are identical or different, R3 represents a hydrogen or a chlorine, R4 and R5, which are identical or different, represent a hydrogen, a C1 to C3 alkyl, or a C1 to C8 alkyl in which a carbon atom is replaced with an oxygen atom, R7 represents a hydrogen, a C1 to C3 alkyl or a fluorine, X represents a sulfur atom, and Z represents a carbon atom or a nitrogen atom.

3. The compound according to claim 1, wherein in the abovementioned formula (I):

A represents

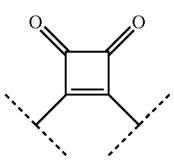
(A1)

B represents

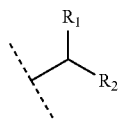
(B1)

R1 represents a C1 to C5 alkyl,

R2 represents:
- a C1 to C5 alkyl,
- a C2 to C5 alkyne, substituted with one or more groups chosen from fluorine and phenyl,
- an aromatic or heteroaromatic ring selected from the group consisting of the rings corresponding to formulae (a), (b1) and (d1) below in which R7 and Z have the meanings given below:

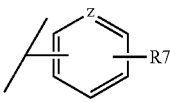
(a)

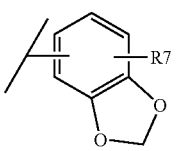
(b1)

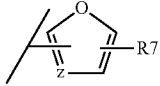
(d1)

R7 can be present several times on a ring, and at most as many times as there are substitutable atoms; the meanings of each substituent R7 are identical or different, R3 represents a hydrogen or a chlorine, R4 and R5, which are identical or different, represent a hydrogen or a C1 to C3 alkyl, R7 represents a hydrogen, a C1 to C3 alkyl or a fluorine, and Z represents a carbon atom or a nitrogen atom.

4. The compound according to claim 1, selected from the group consisting of:

Compound 1: 3-(4-chloro-2-hydroxy-3-methanesulfoximinophenylamino)-4-[(R)-1-(5-methylfuran-2-yl)propylamino]cyclobut-3-ene-1,2-dione;

Compound 2: 3-{4-chloro-2-hydroxy-3-methane[(N-methyl)sulfoximino]phenylaminol-4-[(R)-1-(5-methylfuran-2-yl)propylamino]cyclobut-3-ene-1,2-dione;

Compound 3: 3-{4-chloro-2-hydroxy-3-methane[(N-pyridin-4-yl)sulfoximino]-phenylamino}-4-[(R)-1-(5-methylfuran-2-yl)propylamino]cyclobut-3-ene-1,2-dione;

Compound 4: 3-{4-chloro-2-hydroxy-3-methane[(N-pyridin-4-yl)sulfoximino]-phenylamino}-4-(1-ethylpropylamino)cyclobut-3-ene-1,2-dione;

Compound 5: 3-{4-chloro-2-hydroxy-3-methane[(N-methyl)sulfoximino]phenylamino}-4-{[(S)-(5-methylfuran-2-yl)-(R)-tetrahydrothiophen-2-ylmethyl]amino}cyclobut-3-ene-1,2-dione;

Compound 6: 1-(2-chloro-3-fluorophenyl)-3-(4-chloro-2-hydroxy-3-methanesulfoximinophenyl)urea;

Compound 7: 1-(2-chloro-3-fluorophenyl)-3-{4-chloro-2-hydroxy-3-methane[(N-methyl)sulfoximino]phenyl}urea;

Compound 8: 3-{2-hydroxy-3-methane[(N-methyl)sulfoximino]phenylamino}-4-[(R)-1-(5-methylfuran-2-yl)propylamino]cyclobut-3-ene-1,2-dione;

Compound 9: 3-[4-chloro-3-[N-(2-dimethylaminoethyl)-S-methylsulfonimidoyl]-2-hydroxyanilino]-4-ethoxycyclobut-3-ene-1,2-dione;

Compound 10: 3-[4-chloro-3-[N-(2-dimethylaminoethyl)-S-methylsulfonimidoyl]-2-hydroxyanilino]-4-(1-ethylpropylamino)cyclobut-3-ene-1,2-dione;

Compound 11: 3-[4-chloro-2-hydroxy-3-[N-(2-methoxyethyl)-S-methylsulfonimidoyl]-anilino]-4-[[(1R)-1-(5-methyl-2-furyl)propyl]amino]cyclobut-3-ene-1,2-dione;

Compound 12: (−)-3-{4-chloro-2-hydroxy-3-methane[(N-methyl)sulfoximino]-phenylamino}-4-[(R)-1-(pyridin-2-yl)propylamino]cyclobut-3-ene-1,2-dione;

Compound 13: (+)-3-{4-chloro-2-hydroxy-3-methane[(N-methyl)sulfoximino]-phenylamino}-4-[(R)-1-(pyridin-2-yl)propylamino]cyclobut-3-ene-1,2-dione;

Compound 14: (−)-3-{2-hydroxy-3-methane[(N-methyl)sulfoximino]phenylamino}-4-[(R)-1-(pyridin-2-yl)propylamino]cyclobut-3-ene-1,2-dione;

Compound 15: (−)-3-{2-hydroxy-3-methane[(N-methyl)sulfoximino]phenylamino}-4-[(R)-1-(pyridin-2-yl)propylamino]cyclobut-3-ene-1,2-dione;

Compound 16: (+)-3-{2-hydroxy-3-methane[(N-methyl)sulfoximino]phenylamino}-4-[(R)-1-(5-methylfuran-2-yl)propylamino]cyclobut-3-ene-1,2-dione;

Compound 17: (+)-3-{2-hydroxy-3-methane[(N-methyl)sulfoximino]phenylamino]-4-[(R)-1-(5-methylfuran-2-yl)propylamino]cyclobut-3-ene-1,2-dione;

Compound 18: (−)-3-(2-hydroxy-3-methane[(N-methyl)sulfoximino]phenylamino[4-(1-ethylpropylamino]cyclobut-3-ene-1,2-dione;

Compound 19: (+)-3-(2-hydroxy-3-methane[(N-methyl)sulfoximino]phenylamino[4-(1-ethylpropylamino]cyclobut-3-ene-1,2-dione; and Compound 20: (+)-3-{4-chloro-2-hydroxy-3-methane[(N-methyl)sulfoximino]-phenylamino}-4-[(R)-1-(5-methylfuran-2-yl)propylamino]cyclobut-3-ene-1,2-dione.

5. A pharmaceutical composition comprising an effective amount of a compound or of a pharmaceutically acceptable salt of the compound according to claim 1 in combination with a pharmaceutically acceptable support or solvent.

6. A medicament comprising an effective amount of the compound according to claim 1.

* * * * *